United States Patent [19]

Uehara et al.

[11] Patent Number: 4,959,710

[45] Date of Patent: Sep. 25, 1990

[54] ELECTRONIC ENDOSCOPE WHEREBY THE POSITION OF THE INSERTABLE PART CAN BE KNOWN BY A TRANSMITTED LIGHT OUTSIDE A BODY

[75] Inventors: Masao Uehara; Masahide Kanno; Masahiko Sasaki; Katsuyoshi Sasagawa; Akinobu Uchikubo, all of Hachioji; Jun Hasegawa, Hino; Shinji Yamashita, Hachioji; Katsuyuki Saito, Hachioji; Takehiro Nakagawa, Hachioji, all of Japan

[73] Assignee: Olympus Optical Co., Ltd., Tokyo, Japan

[21] Appl. No.: 311,541

[22] Filed: Feb. 16, 1989

[30] Foreign Application Priority Data

Mar. 1, 1988 [JP] Japan .............................. 63-048361
Jul. 28, 1988 [JP] Japan .............................. 63-188868
Feb. 8, 1989 [JP] Japan .............................. 1-30643
Feb. 9, 1989 [JP] Japan .............................. 1-31943

[51] Int. Cl.⁵ .............................................. H04N 7/18
[52] U.S. Cl. .......................................... 358/98; 128/4; 128/6
[58] Field of Search .................... 358/98; 128/4, 6

[56] References Cited

U.S. PATENT DOCUMENTS 4,706,118 11/1987 Kato et al. .................... 358/98
4,834,070 5/1989 Saitou ............................ 358/98

FOREIGN PATENT DOCUMENTS 60-76888 5/1985 Japan .
61-82731 4/1986 Japan .
62-2927 1/1987 Japan .

Primary Examiner—John K. Peng
Attorney, Agent, or Firm—Armstrong, Nikaido, Marmelstein, Kubovcik & Murray

[57] ABSTRACT

An electronic endoscope apparatus whereby the position of the tip part of an insertable part inserted into a body cavity is confirmed from outside the body with the transmission out of the body from within the body cavity of a light emitted from an illuminating window provided in the tip part. It comprises an imaging apparatus for creating an image of an inspected part obtained from an observing window provided in the tip part of the insertable part and for converting this image to an electric signal and outputting it, an illuminating apparatus for feeding an illuminating light to the imaging apparatus and for adjusting the brightness of the illuminating light when a confirming signal directing to confirm the position of the tip part of the insertable part is input, a signal processing apparatus for processing the electric signal obtained from the imaging apparatus, outputting a video signal which is a normal observing picture image signal of a moving picture in case the confirming signal is not input and outputting a video signal which is a picture image signal different from the ordinary observing picture image signal in case the confirming signal is input, and a displaying apparatus for receiving the video signal output by the signal processing apparatus and displaying the picture image of the inspected part.

27 Claims, 36 Drawing Sheets

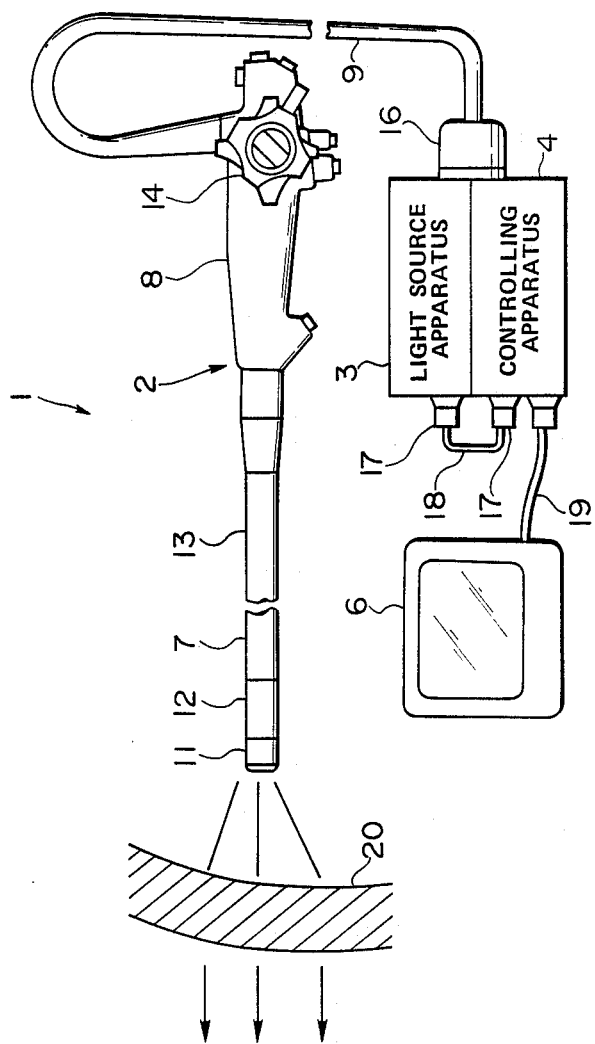

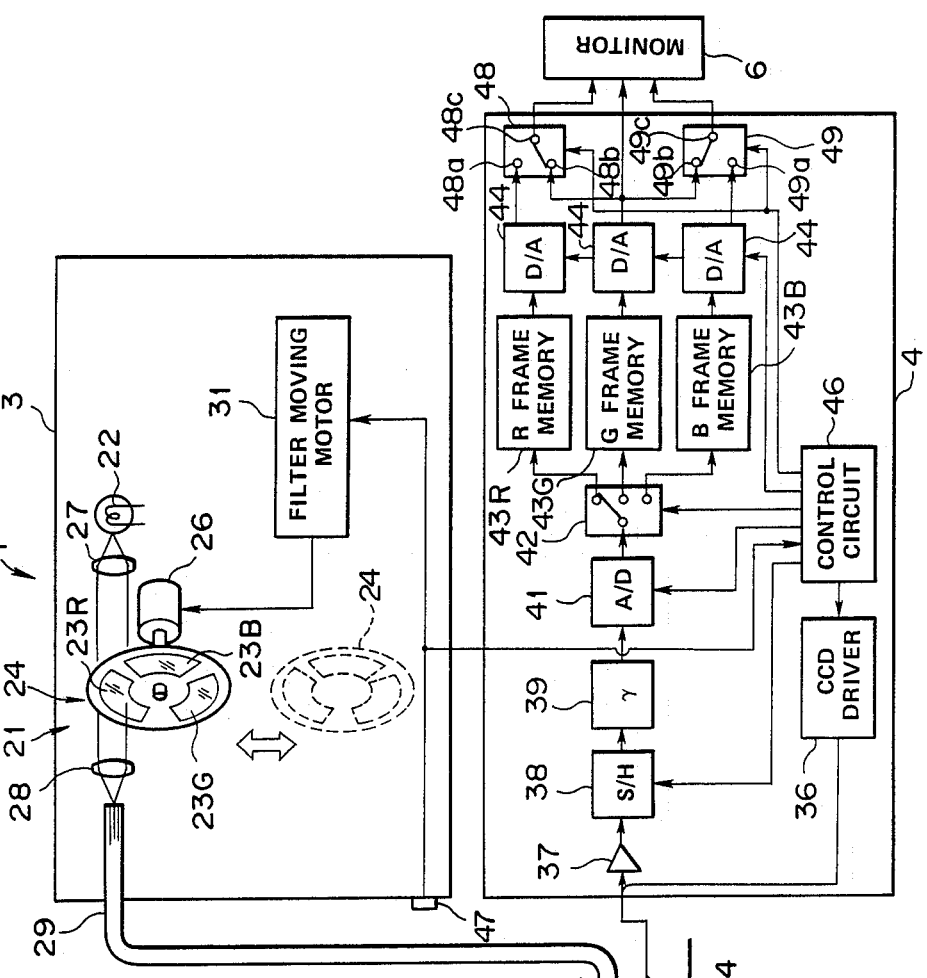
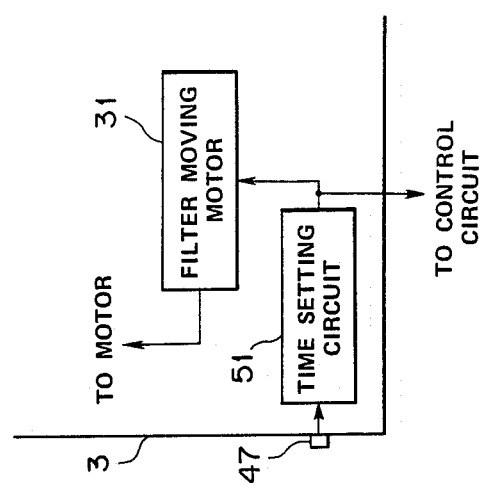

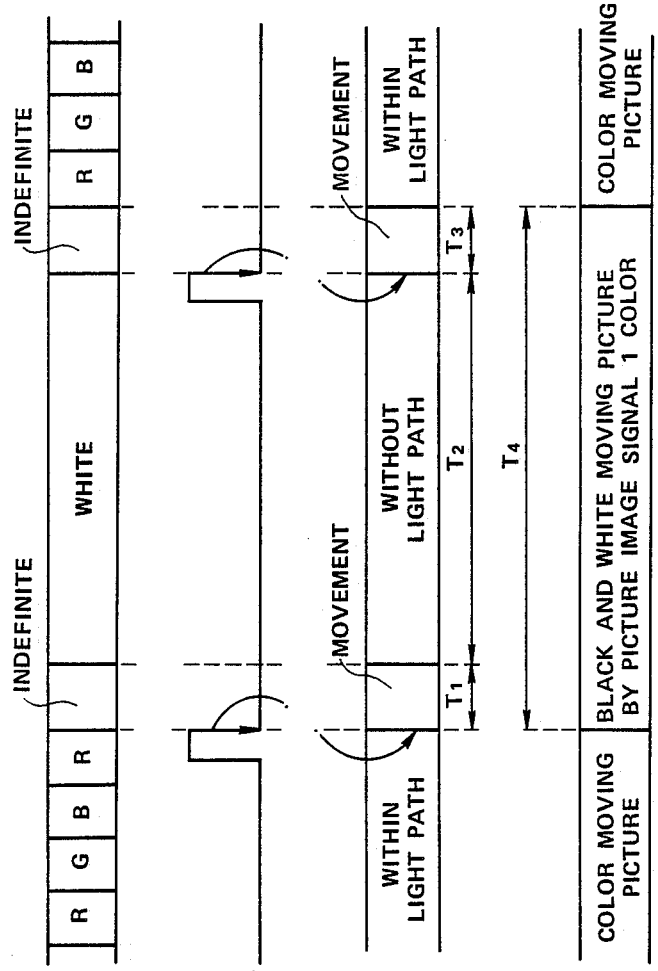

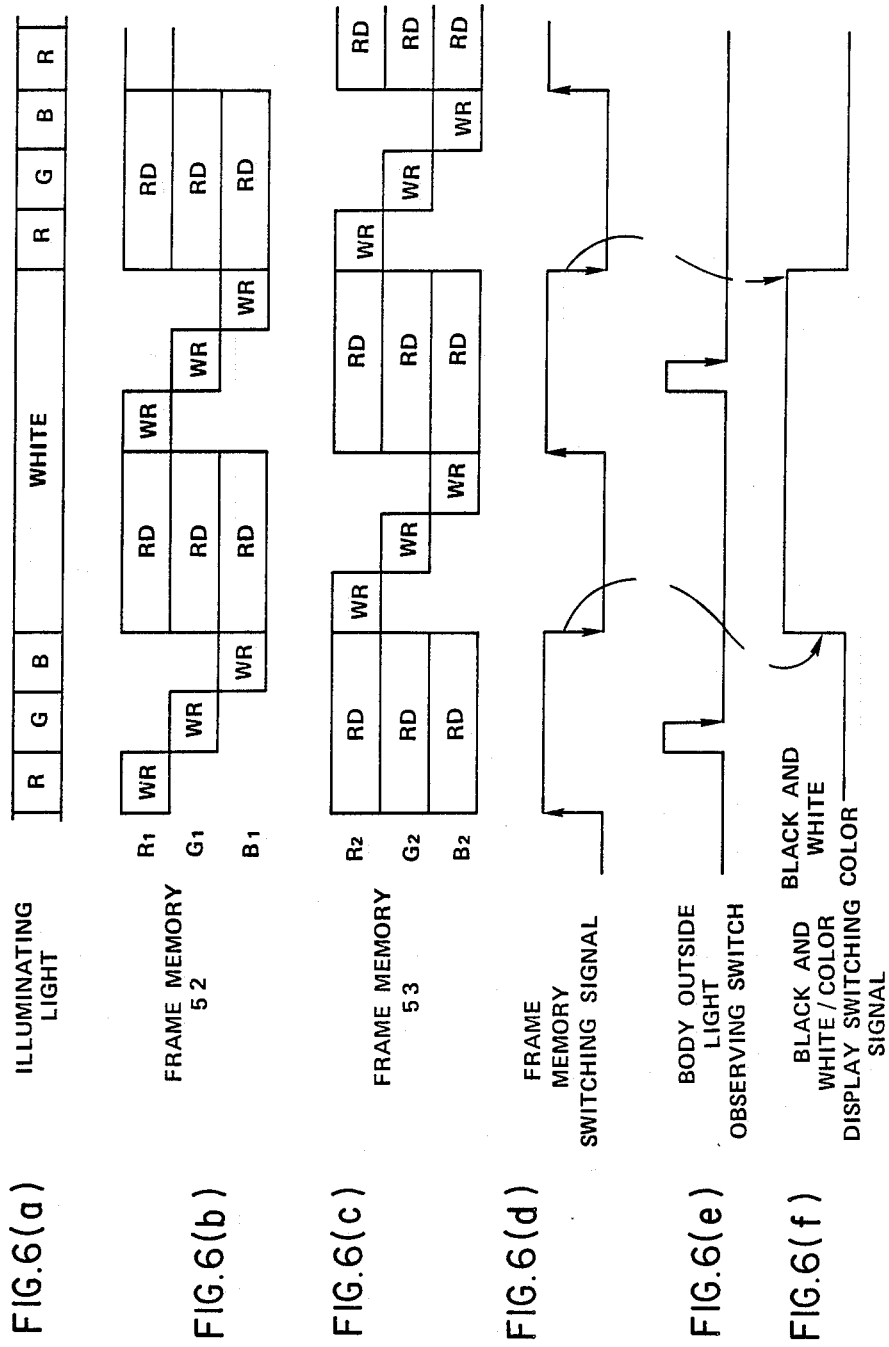

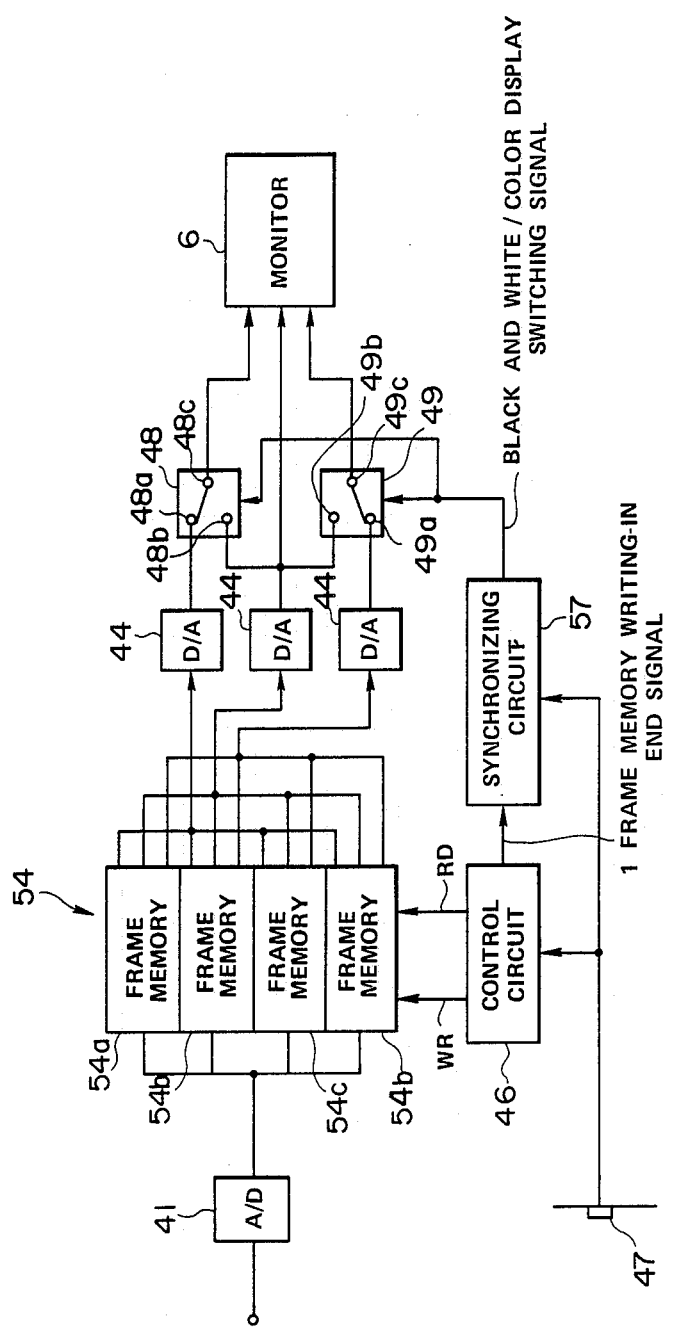

| R | G | B | WHITE | | | | | | R |
|---|---|---|---|---|---|---|---|---|---|
| R₁ | R₁ | R₁ | R₁ | | G₂ | G₂ | G₂ | G₂ | |
| R₀ | G₁ | G₁ | G₁ | | G₁ | B₂ | B₂ | B₂ | G₂ |
| G₀ | B₁ | B₁ | B₁ | | B₁ | B₁ | R₃ | R₃ | B₂ |
| B₀ | B₀ | R₂ | R₂ | | R₂ | R₂ | R₂ | G₃ | R₃ |

FIG.8(a) ILLUMINATING LIGHT

FIG.8(c) 1 FRAME MEMORY WRITING-IN END SIGNAL

FIG.8(d) BODY OUTSIDE LIGHT OBSERVING SWITCH

FIG.8(e) BLACK AND WHITE / COLOR DISPLAY SWITCHING SIGNAL

BLACK AND WHITE
COLOR

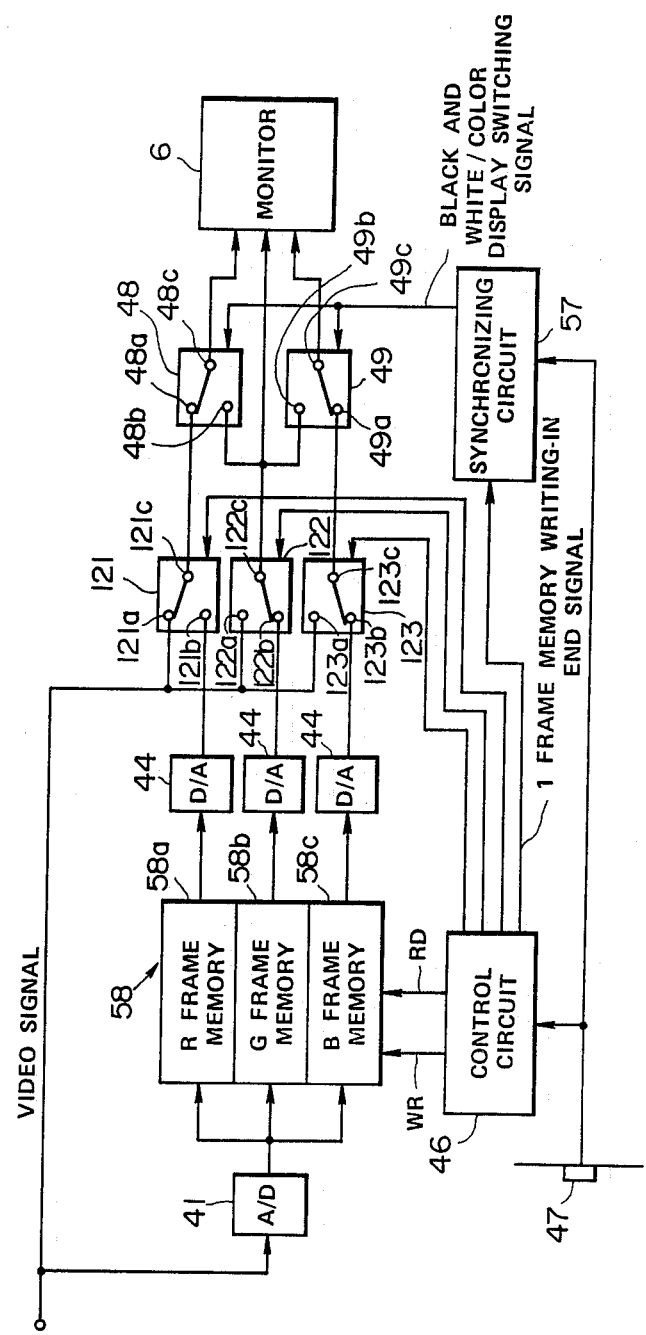

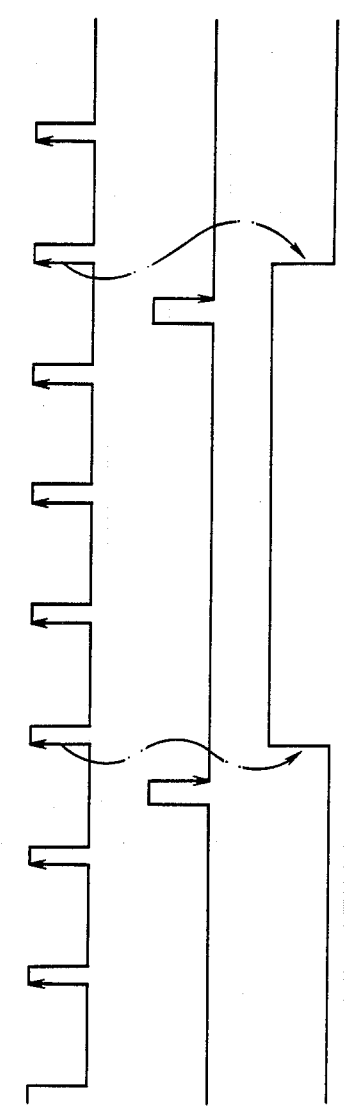

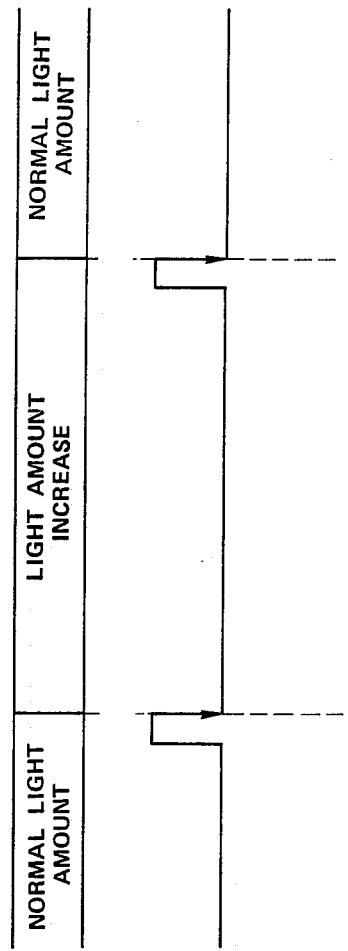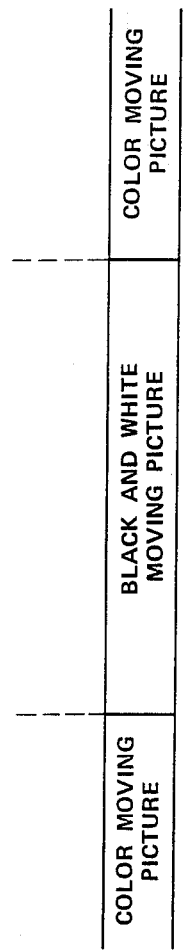
FIG. 12(a) ILLUMINATING LIGHT
FIG. 12(b) BODY OUTSIDE LIGHT OBSERVING SWITCH
FIG. 12(c) MONITOR PICTURE IMAGE

FIG.15
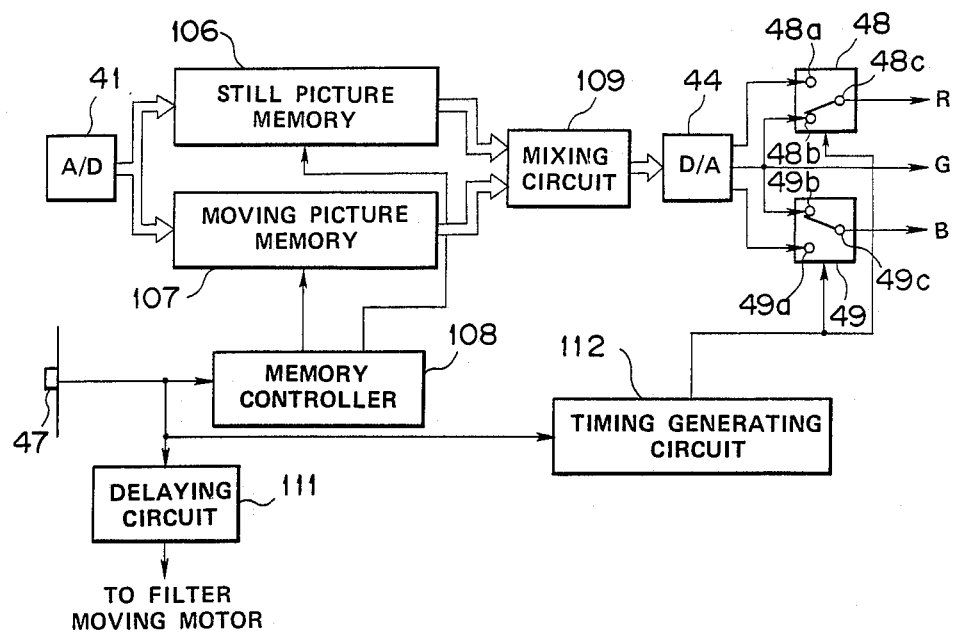
FIG. 16(a)
MONITOR DISPLAY PICTURE IMAGE
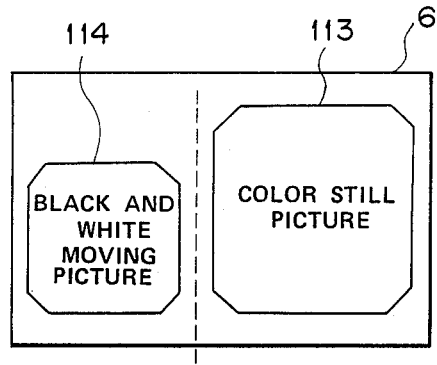
FIG. 16(b)
SWITCHING SWITCH TIMING SIGNAL

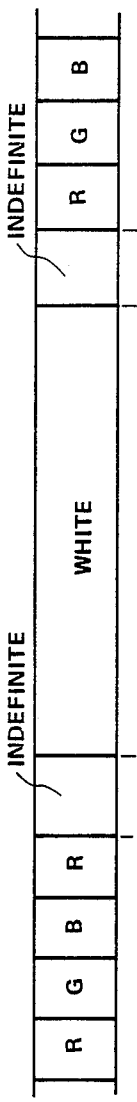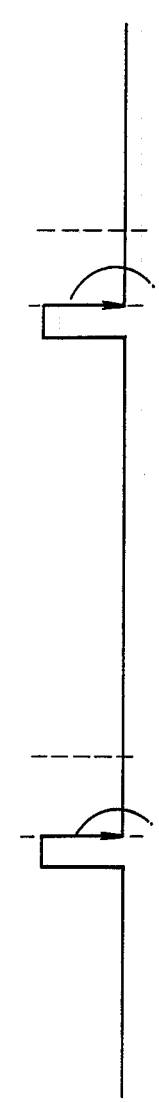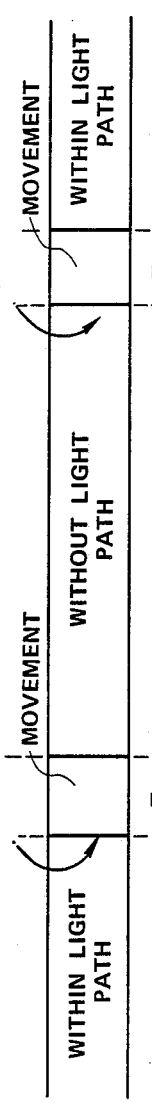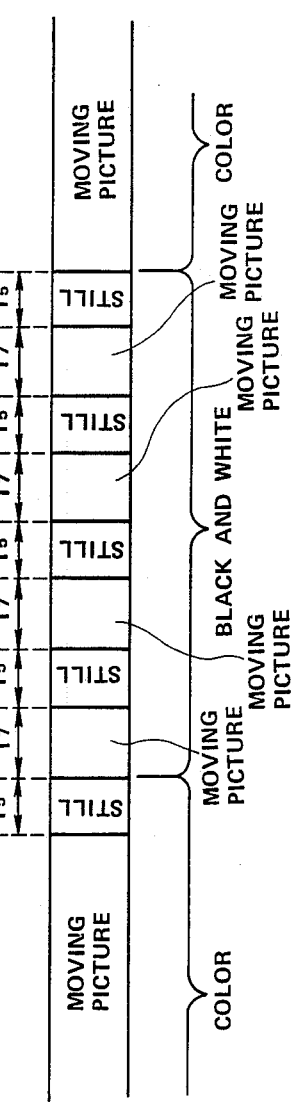
FIG.22(a) ILLUMINATING LIGHT
FIG.22(b) BODY OUTSIDE LIGHT OBSERVING SWITCH
FIG.22(c) FILTER POSITION
FIG.22(d) FLASHING SIGNAL
FIG.22(e) MONITOR PICTURE IMAGE

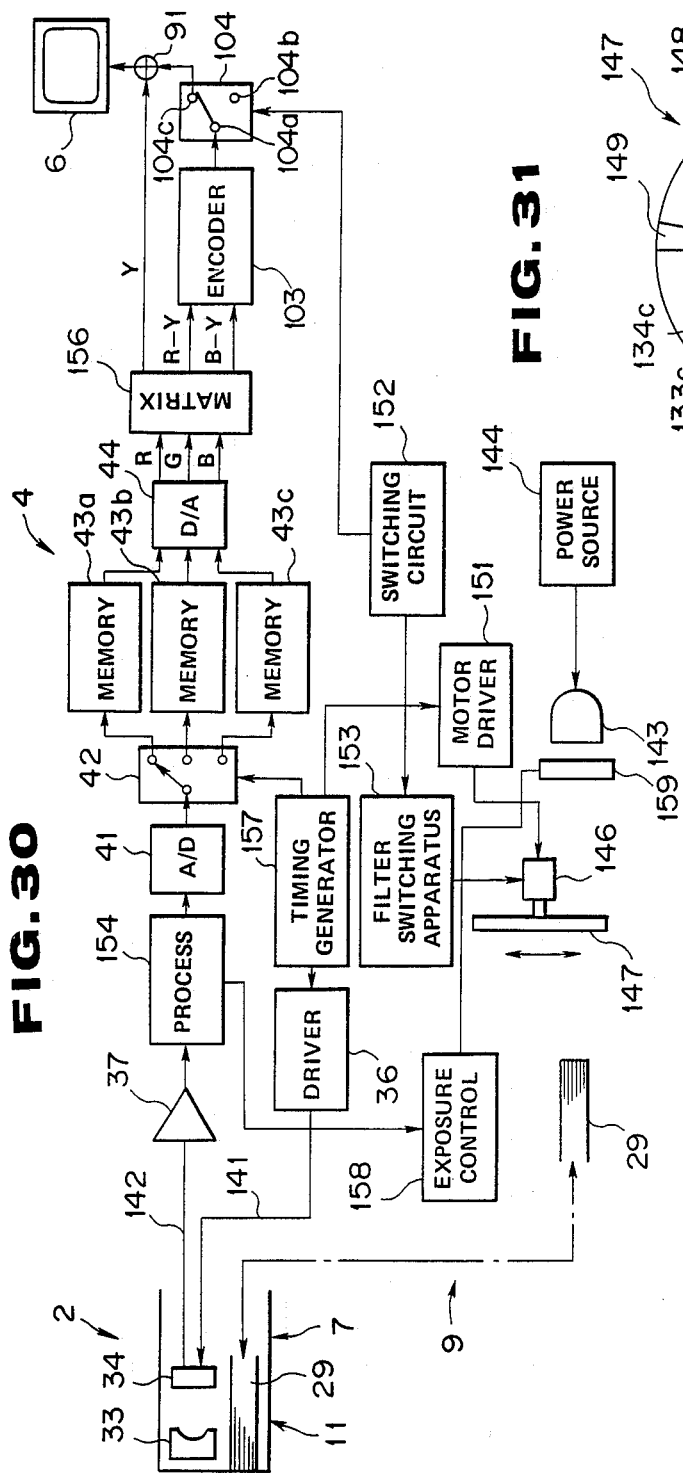
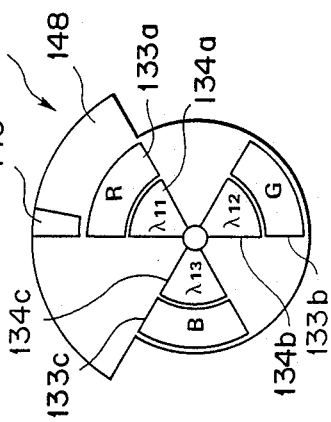
FIG. 30
FIG. 31

ELECTRONIC ENDOSCOPE WHEREBY THE POSITION OF THE INSERTABLE PART CAN BE KNOWN BY A TRANSMITTED LIGHT OUTSIDE A BODY

FIELD OF THE INVENTION

This invention relates to an electronic endoscope whereby the position of the tip part of the endoscope insertable part can be confirmed by a transmitted light outside a body.

BACKGROUND OF THE INVENTION

Recently, there is extensively utilized an endoscope (called also a scope or fiber scope) whereby, by inserting an elongate insertable part into a body cavity, organs within the body cavity can be observed or, as required, by using a treating tool inserted through a treating tool channel, various therapeutic treatments can be made.

Also, there are suggested various electronic scopes wherein such solid state imaging device as a charge coupled device (CCD) is used for an imaging means.

In the color picture image imaging system of such electronic scope, there are such frame sequential type wherein an illuminating light is sequentially switched to R (red), G (green) and B (blue) as is shown, for example in the publication Of Japanese Patent Application Laid Open No. 82731/1986 and such color mosaic type (called also a simultaneous type) wherein a filter array in which color transmitting filters transmitting respectively color lights of R, G and B are arrayed is provided on the front surface of a solid state imaging device as is shown in the publication of Japanese Patent Application Laid Open No. 76888/1985.

Now, in the frame sequential type electronic scope, as the illuminating light illuminating an object is transmitted through color separating filters of R (red), G (green) and B (blue) to be separated into the respective colors, the illuminating light amount will reduce to be lower than in the color mosaic type radiating a white light to the object and, in the case of confirming the tip position of the electronic scope by the transmitted light outside the body, the illuminating light amount will be so small as to make it hard to confirm the tip position. In order to solve this problem, as shown, for example, in the publication of Japanese Patent Application Laid Open No. 2927/1982, there is disclosed a technique of increasing the light amount by removing the color separating filters from the light path even when the frame sequential type electronic scope is used. However, the monitor image in this case will be neither an intrinsic color picture image nor a black and white picture image while the color separating filters are moved out of the light path from within the light path or, on the contrary, into the light path from outside the light path. Further, by the movement of the organ within the body, a so-called color smear will be produced in the picture image. There have been such problems.

On the other hand, in the mosaic type electronic scope, in case the position of the tip part is hard to recognize, the light amount of the light source apparatus may be increased but, when it is increased, as the primary color signals of R and B are superimposed as modulated carrier signals on the color signal G or luminance signal Y, the output signal of the solid state imaging device will quickly saturate the color signal components and, as a result, will produce a skipped color picture image very hard to see as an observed picture image.

OBJECT AND SUMMARY OF THE INVENTION

An object of the present invention is to provide an electronic endoscope apparatus to obtain a picture image having no color smear and color skip and easy to see even when the tip position is recognized from outside by a transmitted light, and which has improved in the safety and operatability.

An electronic endoscope apparatus according to the present invention comprises an imaging apparatus for producing the image of an inspected part obtained through an observing window provided in the tip part of an insertable part, converting this image to an electric signal and outputting the electric signal, an illuminating apparatus for feeding an illuminating light to the imaging apparatus and adjusting the light amount of the illuminating light when a confirming signal to confirm the position of the tip part of the insertable part is input, a signal processing apparatus for processing the electric signal obtained from the imaging apparatus, outputting a video signal which is an ordinary observing picture image of a moving picture in case a confirming signal is not input and outputting a video signal which is a picture image different from the ordinary observing picture image in case the confirming signal is input and a displaying apparatus receiving the video signal output from the signal processing apparatus and displaying the picture image of the inspected part.

The other features and advantages will become apparent with the following explanation.

BRIEF DESCRIPTION OF THE DRAWINGS

FIGS. 1 to 6 relate to the first embodiment of the present invention.

FIG. 1 is an explanatory view of an entire electronic endoscope apparatus.

FIG. 2 is a block diagram showing the formation of the entire electronic endoscope.

FIGS. 3(a)–3(d) are is a timing chart views for explaining the operation of the electronic endoscope apparatus.

FIG. 4 is a block diagram for explaining the case of providing a time setting circuit.

FIG. 5 is a block diagram showing the formation of a frame memory.

FIGS. 6(a)–6(f) are timing chart views for explaining the operation in FIG. 5.

FIG. 7 is a modification of the first embodiment and is a block diagram showing the formation of a frame memory.

FIGS. 8(a)–8(e) are timing chart views for explaining the operation in FIG. 7.

FIG. 9 is another modification of the first embodiment and is a block diagram showing the formation of a frame memory.

FIGS. 10(a)–10(h) are timing chart views for explaining the operation in FIG. 9.

FIGS. 11 and 12 relate to the second embodiment of the present invention.

FIG. 11 is a block diagram showing the formation of an entire electronic endoscope apparatus.

FIGS. 12(a)–12(c) are timing chart views for explaining the operation in FIG. 11.

FIG. 13 is a block diagram showing the formation of an entire electronic endoscope apparatus.

FIGS. 14(a)–14(c) are a timing chart view for explaining the operation in FIG. 13.

FIGS. 15 and 16 relate to the fourth embodiment of the present invention.

FIG. 15 is a block diagram for explaining the formation of an electronic endoscope apparatus.

FIGS. 16(a) and 16(b) are explanatory views of a switching switch and the timing of a monitor picture image.

FIG. 17 is a block diagram for explaining the formation of an electronic endoscope apparatus.

FIGS. 18(a)–18(d) are timing chart views for explaining the operation in FIG. 17.

FIG. 19 is a block diagram for explaining the formation of an electronic endoscope apparatus.

FIGS. 20(a)–20(e) are timing chart views for explaining the operation in FIG. 191

FIGS. 21 and 22 relate to the seventh embodiment of the present invention.

FIG. 21 is a block diagram for explaining the formation of an electronic endoscope apparatus.

FIGS. 22(a)–22(e) are timing chart views for explaining the operation in FIG. 21.

FIG. 23 is a block diagram for explaining the formation of an electronic endoscope apparatus.

FIG. 24 is a timing chart view for explaining FIG. 23.

FIG. 25 is a block diagram for explaining the formation of an electronic endoscope apparatus.

FIG. 26 is a contour view of a rotary filter for normal observation.

FIG. 27 is a contour view of a rotary filter for special observation.

FIG. 28 is an explanatory view showing a spectral transmitting characteristic of a rotary filter for normal observation.

FIG. 29 is an explanatory view showing a spectral transmitting characteristic of a rotary filter for special observation.

FIGS. 30 and 32 relate to the tenth embodiment of the present invention.

FIG. 30 is a block diagram showing the formation of an electronic endoscope apparatus.

FIG. 31 is a contour view of a rotary filter.

FIG. 32 is an explanatory view showing a transmitted wavelength band of a filter for special observation.

FIG. 33 is a block diagram showing the formation of an electronic endoscope apparatus.

FIG. 34 is an explanatory view of a rotary filter.

FIG. 35 is a block diagram showing the formation of an electronic endoscope apparatus.

FIG. 38 is an explanatory view of an entire electronic endoscope apparatus.

DETAILED DESCRIPTION OF PREFERRED EMBODIMENTS OF THE INVENTION

Figure 5:
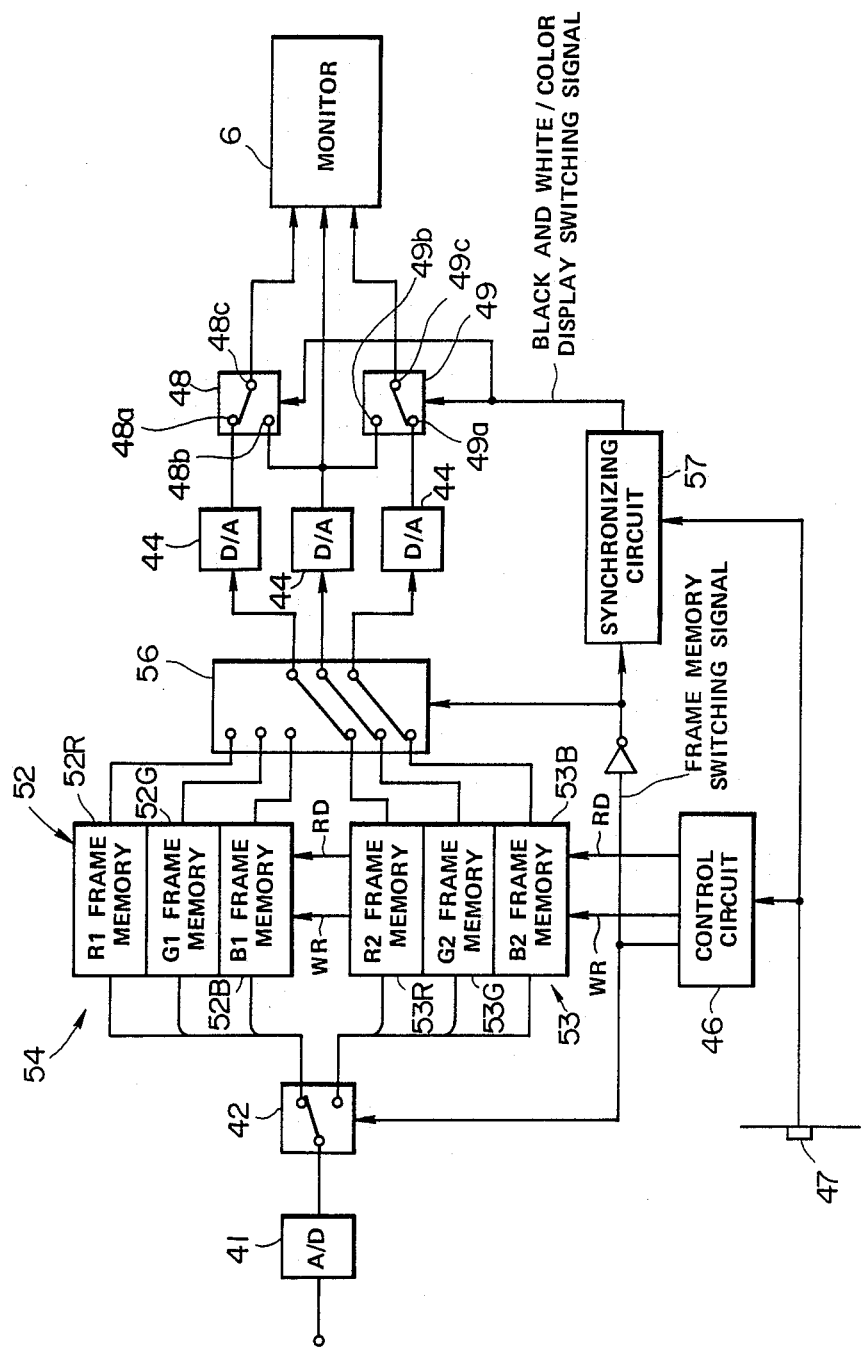

The embodiments of the present invention shall be explained in the following with reference to the drawings.

FIGS. 1 to 4 show the first embodiment of the present invention.

In FIG. 1, an electronic endoscope 1 comprises an endoscope 2, a light source apparatus 3 for feeding an illuminating light to this endoscope, a controlling apparatus 4 for processing the output signal of the endoscope 2 and a monitor 6 for displaying on a picture surface the video signal output from this controlling apparatus.

The above mentioned endoscope 2 is provided with an elongate insertable part 7, a thick operating part 8 connected to the rear end side of this insertable part 7 and a light guide and signal cable 9 extended from the side of this operating part 8.

A rigid tip part 11 is provided on the tip side of the above mentioned insertable part 7 and a curvable part 12 is provided on the rear side adjacent to this tip part 11. Further, a flexible part 13 is connected to this curvable part 12 in the rear. The above mentioned curvable part 12 can be curved in the vertical/horizontal direction by operating a curving operation knob 14 provided on the above mentioned operating part 8.

A light guide and signal cable connector 16 is provided at the rear end of the above mentioned light guide and signal cable 9 so as to be connected simultaneously to the above mentioned light source apparatus 3 and controlling apparatus 4. These light source apparatus 3 and controlling apparatus 4 are connected with each other through a signal cable 18 provided with connectors 17 at both ends. Further, the controlling apparatus 4 is connected to the above mentioned monitor 6 through a signal cable 19.

The illuminating light fed from the above mentioned light source apparatus 3 is emitted forward from the tip part 11 and passes partly through an inner wall 20 of the body cavity.

In FIG. 2, a light source part 21 provided within the above mentioned light source apparatus 3 is provided with a light source lamp 22 and a rotary color filter 24 having color transmitting filters 23R, 23G and 23B of three primary colors of R (red), G (green) and B (blue). This rotary color filter 24 is rotated and driven by a motor 26. The illuminating light emitted by the above mentioned light source lamp is made a parallel light beam by a condensing lens 27 and enters the above mentioned rotary color filter 24. The illuminating light passing through this rotary color filter 24 is made color lights of respective wavelengths of red, green and blue which are condensed by a condenser lens 28 and enter the light guide 29 on the entrance end surface.

The above mentioned rotary color filter 24 can be inserted into and removed from the light path connecting the light source lamp 22 and the light guide 29 on the entrance end surface with each other by a filter moving motor 31.

The above mentioned light guide 29 is inserted through the endoscope 2 and can radiate the illuminating light onto the inner wall 20 of the body cavity through a light distributing lens 32 arranged forward of the exit end surface of this light guide 29.

The reflected lights corresponding to the respective color lights of red, green and blue from the above mentioned body cavity inner wall pass through an objective lens 33 and are received on the imaging surface of a solid state imaging device (which shall be abbreviated as CCD hereinafter) 34 provided in the image forming position of this objective lens 33. The object image is photoelectrically converted by this CCD 34 and is sequentially output, for example, in the horizontal direction by a driving clock applied from a CCD driver 36 provided within the controlling apparatus 4. This electric signal including the picture image information is input into a preamplifier 37 within the above mentioned controlling apparatus 4. The electric signal amplified and impedance-converted by this preamplifier 37 has frame sequential video signals B, G and R extracted by a sample holding circuit 38, is further γ corrected by a γ correcting circuit 39 and is then converted to a digital signal by an A/D converter 41. This electric signal is synchronized with a color frame sequential illuminating light by a multiplexer 42 and is written sequentially into an R frame memory 43R, G frame memory 43G and B frame memory 43B which are memories synchronizing the frame sequential signals corresponding to the respective colors of red, green and blue. These respective frame memories 43R, 43G and 43B are simultaneously read out in the horizontal direction at a speed matching the monitor 6 and are respectively converted to analogue signals by a D/A converter 44 to be synchronized three primary color signals of R, G and B.

The above mentioned analogized color signal R is connected to be input into the input terminal 48a of a switch 48 of two inputs and one output as a selecting means. The color signal B is connected to be input into the input terminal 49a of a switch 49 of two inputs and one output as a selecting means.

Further, the color signal G is branched and is connected to be input into the input terminal 48b of the switch 48, the input terminal 49b of the switch 49 and the monitor 6.

The output terminals 48c and 49c of the switches 48 and 49 of two input and one output are connected to the above mentioned monitor 6. In this monitor 6, in case the input terminals 48a and 49a are selected by the switches 48 and 49, a color picture image which is a normal observing picture image will be displayed but, in case the input terminals 48b and 49b are selected, a black and white moving picture image produced by the color signal G monochrome which is a picture image different from the normal observing picture image will be displayed.

A control circuit 46 for controlling the timing of the entire signal processing circuit is provided within the above mentioned controlling apparatus 4, and controls the timing of a driving clock applied to the CCD 34 by the voltage level converted by the CCD driver 36 and inputs sampling pulses into the sample holding circuit 38 for extracting a video signal from the electric signal read out by this driving clock.

Also, this control circuit 46 controls the converting speed of the A/D converter 41, writing and reading data into and out of the respective frame memories 43R, 43G and 43B of the multiplexer 42 and the converting speed of the D/A converter 44.

On-off-signals are input into the above mentioned control circuit 46 from a body outside light observing switch 47 provided in the light source apparatus together with the above mentioned filter moving motor 31. In the control circuit 46, when an on-signal is input, the input terminal 48b and 49b sides of the output switches 48 and 49 of two inputs and one output will be selected and a color signal G will be output to the monitor 6. When an on-signal is input into the filter moving motor 31, the rotary color filter 24 will be retreated from the light path connecting the light source lamp 22 and the entrance end surface of the light guide 29. Further, when the body outside light observing switch 47 is switched off, the rotary color filter 24 will be inserted into the light path by the filter moving motor 31, then the input terminal 48a and 49a sides of the switches 48 and 49 of two inputs and one output will be selected by the control circuit 46, the color signals R, G and B will be input into the monitor 6 and a color moving picture which is a normal observing picture image will be displayed.

The operation of the electronic endoscope apparatus formed as in the above shall be explained with reference to the timing chart view in FIG. 3.

The operator inserts the insertable part 7 of the endoscope 2 into a body cavity. The illuminating light emitted from the light source apparatus 3 is fed to the light guide 29 as sequentially separated into respective color lights of R (red), G (green) and B (blue) as in FIG. 3.

During the inserting operation, in order to confirm the position of the tip part 11, the operator switches on the body outside light observing switch 47 provided in the light source apparatus 3. By this on-signal, the filter moving motor 31 is started to drive and the rotary color filter 24 begins to retreat from the light path as in (c) in FIG. 3. In this moving period $T_1$, the illuminating light is indefinite. At the time point when the movement of the rotary color filter 24 is completed, the illuminating light will become a white light of an increased brightness and the position of the tip part 11 will be easily confirmed by the light transmitted from within the body. By on-signal of the body outside light observing switch 47, the input terminal 48b and 49b sides of the switches 48 and 49 of two inputs and one output are selected by the control circuit 46.

When the above mentioned rotary color filter 24 is retreated from the light path, the observed image by the white light of the body cavity inner wall 20 will be formed on the imaging surface of the solid state imaging device 34 through the objective lens 33 but, as the solid state imaging device 34 is fundamentally a black and white image sensor, a frame sequential video signal which is different from the frame sequential signal of color signals R, G and B at the time of the ordinary observation and contains intrinsically no color information will be obtained, will be then processed the same as at the time of the ordinary observation, will be analogue-converted and will be input into the switches 48 and 49 of two inputs and one output. As the input terminals 48b and 49b of these switching switches 48 and 49 of two inputs and one output are selected, the input signal of the monitor 6 will be only the color signal G and, under whatever circumstances, a moving picture of a black and white picture image produced by a G monochrome different from the ordinary observing picture image will be stably displayed and no color smear will be produced.

Next, after the period $T_4$ when the confirmation of the tip position by the body outside transmitted light ends, the operator again pushes the body outside light observing switch 47 to be off. By this off-signal, the rotary color filter having retreated out of the light path will begin to move into the light path. When the movement ends after the moving period $T_3$ and the illuminating light changes to R (red), G (green) and B (blue) separated from the white light, the input terminal 48a and 49b sides of the switches 48 and 49 will be selected by the control circuit 46. The observed image illuminated by the respective color lights of R (red), G (green) and B (blue) is formed on the solid state imaging device 34, is converted to an electric signal and is processed to produce color signals R, G and B which are analogized by the D/A converters 44 and are output to the monitor 6 through the switching switches 48 and 49 of two inputs and one output. The monitor 6 displays on a picture surface a color moving picture which is an ordinary observing picture image.

In the above mentioned embodiment, the picture image different from the ordinary observing picture image is a black and white display by a G monochrome. However, it is needless to say that the picture image is not limited to the G signal but either of the color signals R and B will do. If the wiring of the switches 48 and 49 of two inputs and one output is to be changed, it will be able to be easily attained.

In this embodiment, the body outside observing switch 47 is of an alternate type which will be on when pushed for the first time and will be off when pushed for the second time. However, it is easy that, once pushed, during any set time, the above mentioned light amount will be increased. Its formation is shown in FIG. 4 in which the body outside observing switch 47 can input the on-signal into a time setting circuit 51 which may be controlled, for example, by a CPU the same as a monostable multivibrator or a counter type by the counting of a reference clock. Simultaneously with the beginning of the counting, the time setting circuit 51 in which the on-signal has been input will output a control signal to the filter moving motor 31 so as to retreat the rotary color filter 24 from the light path. Further, the on-signal is input into the control circuit 46, operates as mentioned above and switches the switches 48 and 49. When the time setting circuit 51 counts the count number corresponding to the preset time, a control signal will be transmitted to the filter moving motor 31 and the rotary color filter 24 will be interposed in the light path.

As mentioned above, in this embodiment, as the picture image signal input into the monitor 6 by the switches 48 and 49 of two inputs and one output is made a G monochrome during the period $T_4$ which is the total of the periods $T_1$ and $T_3$ when the rotary color filter 24 moves and the period $T_2$ when the rotary color filter 24 is fixed out of the light path, in case the color signal is indefinite due to the illuminating light when the rotary color filter 24 is moved and in case the illuminating light becomes white after the rotary color filter 24 is retreated, a picture image having no color smear by the movement of the object within the body and easy to see will be able to be provided.

By the way, the frame memory may be formed as in FIG. 5.

In FIG. 5, a memory part 54 consisting of two frame memory parts 52 and 53 is connected to the rear of the multiplexer 42. This one frame memory 52 is provided with an $R_1$ frame memory 52R, $G_1$ frame memory 52G and $B_1$ and $B_1$ frame memory 52B into which color signals of R, G and B are to be respectively written in. The other frame memory 53 is provided with an R2 frame memory 53R, G2 frame memory 53G and B2 frame memory 53B.

A switch 56 is provided in the rear of this memory part 54 so that the color signals read out of the respective frame memories 52 and 53 may be input into six input terminals provided in this switch 56. This switch 56 selects the frame memory 52 or 53 and outputs the color signal from the selected frame memory 52 or 53 simultaneously to the D/A converters 44. The circuit formation after the D/A converters 44 is the same as in FIG. 2.

The control circuit 46 outputs a frame switching signal to the multiplexer 42. This frame switching signal is inverted and is output to the switch 56 and synchronizing circuit 57. The multiplexer 42 selects the frame memory 52 or 53 into which R, G and B color signals are to be written by this frame switching signal and the switch 56 reads the R, G and B color signals out of the frame memory 52 or 53 not selected by the multiplexer 42. The control circuit 46 outputs a light signal to the frame memory 52 or 53 selected (written in) by the multiplexer 42 and at the same time outputs a reading signal to the frame memory 52 or 53 not selected (read out).

Signals from the respective body outside light observing switch 47 are input into the control circuit 46 and synchronizing circuit 57. When the signal from the body outside light observing switch 47 is input, the synchronizing circuit 57 will output a black and white/color display switching signal to the switching switches 48 and 49 of two inputs and one output immediately after the frame memory switching signal is input.

The operation in FIG. 5 shall be explained by using FIG. 6.

In the memory part 54, two frame memories 52 and 53 are alternately writing in and reading out. That is to say, such frame memory switching signal as is shown in FIG. 6(d) is output to the multiplexer 42 from the control circuit 46. For example, by the rise of the frame switching signal, the multiplexer 42 selects the frame memory 52 and writes the R, G and B color signals into the memories 52R, 52G and 52B and, by the fall, it selects the frame memory 53 and writes the R, G and B color signals into the memories 53R, 53G and 53B. By the rise of the inverted frame memory switching signal, the switch 56 selects the frame memory 52 and simultaneously reads the R, G and B color signals out of the respective memories 52R, 52G and 52B and, by the fall, the switch 56 selects the frame memory 53 and simultaneously reads the R, G and B color signals out of the respective memories 53R, 53G and 53B. Thus, the multiplexer 42 and switch 56 repeat selecting the frame memories 52 and 53 different from each other and output to the monitor 6 the read R, G and B color signals through the D/A converters 44 and output switches 48 and 49 of two inputs and one output.

When the body outside light observing switch 47 is switched on in order to confirm the position of the tip part 11 of the insertable part 7, this on-signal will be input into the filter moving motor 31 (FIG. 2), control circuit 46 and synchronizing circuit 57. By this on-signal, the filter moving motor 31 will move and the illuminating light will become white. Just after this on-signal, as synchronized with the rise or fall of the frame memory switching signal, the black and white/color display switching signal shown in FIG. 6(f) is output to the switches 48 and 49 of two inputs and one output. By this black and white/color display switching signal, the switch 48 selects the input terminal 48b and the switch 49 selects the input terminal 49b and, in the state in FIG. 5, the color signal of the $G_2$, frame memory 53G is output to the monitor 6. In the monitor 6, as the input signal is only the G signal, a moving picture of a black and white picture image by the G monochrome different from the ordinary observing picture image is stably displayed and no color smear is produced.

When the confirmation of the position of the tip part 11 ends, an on-signal will be again input from the body outside light observing switch 47. By this on-signal, the filter moving motor moves the rotary filter 24 into the light path. Thereby, the illuminating light becomes sequential lights of R, G and B color lights.

As synchronized with the rise or fall of the frame memory switching signal just after the on-signal is input, the synchronizing circuit 57 switches off the black and white/color display switching signal so far output. By this switching off, the switches 48 and 49 of two inputs and one output select the input terminals 48a and 49a and output R, G and B color signals to the monitor 6 from the frame memory 52 or 53. An endoscope image which is a moving picture of a color picture image which is an ordinary observing picture image is displayed in the monitor 6.

FIGS. 7 and 8 show a modification of the first embodiment.

This modification corresponds to FIGS. 5 and 6 and the memory part 54 is formed of one group of frame memories in this modification but is formed of two groups of frame memories 52 and 53 in FIG. 5.

By the way, the formation of the front steps from the memory part 54 is the same as in the first embodiment.

In this modification, the memory part 54 is formed of four frame memories 54a, 54b, 54c and 54d. The multiplexer 42 is not provided. Writing into and reading out of the memory part 54 are made by a reading signal and writing signal from the control circuit 46. Color signals read out by the writing signal are output simultaneously to the D/A converters and come to the monitor 6 through the switches 48 and 49. The same as in FIG. 5, the switching switches 48 and 49 are controlled in switching by a black and white/color display switching signal output from the synchronizing circuit 57 but a black and white/color display switching signal is output from the synchronizing circuit 57 by a one-frame memory writing-in end signal input from the control circuit 46.

The other formations are the same as in the first embodiment.

The operation in FIG. 7 shall be explained by using FIG. 8.

Digital-converted R, G and B color signals are sequentially transmitted from the A/D converter 41. For example, if the color signal R1 is transmitted, the control circuit 46 will output a writing signal to the frame memory 54a and will write the color signal $R_1$ into the frame memory 54. At the same time, the control circuit 46 outputs reading signals to the other frame memories 54b, 54c and 54d and read color signals $R_0$, $G_0$ and B respectively out of these memories 54b, 54c and 54d. By the way, in FIG. 8(b), the circle ( ) mark represents that the frame memory 54 is in a reading state.

When a color signal $G_1$ is then transmitted from the A/D converter 41, the control circuit 46 will output a writing signal to the frame memory 54b and will write the color signal $G_1$ into the frame memory 54b. At the same time, the control circuit 46 outputs reading signals respectively to the frame memories 54a, 54c and 54d and reads color signals $R_1$, G and B respectively out of these frame memories 54a, 54c and 54d.

When a color signal $B_1$ is then transmitted from the A/D converter 41, the control circuit 46 will output a writing signal to the frame memory 54 and will write a color signal $B_1$ into the frame memory 54c. At the same time, the control circuit 46 outputs reading signals to the other frame memories 54a, 54b and 54d and reads color signals $R_1$, $G_1$ and B respectively out of these frame memories 54a, 54b and 54d.

Thus, any one of the four frame memories 54a, 54b, 54c and 54d is always in the writing-in state and the other three are in the reading-out state.

The control circuit 46 outputs writing signals and reading signals to the memory part 54 as mentioned above and, for example, when the writing of the color signal $R_1$ into the frame memory 54a ends, as in FIG. 6(c), a one-frame memory writing-in end signal will be output to the synchronizing circuit 5 from the control circuit 46.

When an on-signal from the body outside light observing switch 47 is input as in FIG. 6(d), as synchronized with the rise of the one-frame memory writing-in end signal input just after this on-signal, the synchronizing circuit 57 will switch on the black and white/color display switching signal as in FIG. 6(e). This black and white/color display switching signal is input into the switches 48 and 49 and is switched as described in the first embodiment. Thereby, a picture image of a black and white moving picture by a monochrome which is a picture image different from a normal observing picture is displayed in the monitor 6.

When the confirmation of the tip part 11 ends and an on-signal is again input from the body outside light observing switch 47, as synchronized with the rise of the one-frame writing-in end signal just after this on-signal, the synchronizing circuit 57 will switch off the black and white/color display switching signal which is in the on-state. The switches 48 and 49 are switched by this off-signal and a moving picture of a color picture image of a normal observing picture image will be displayed in the monitor 6.

The other formations and effects are the same as in the first embodiment.

FIGS. 9 and 10 are of another modification of the first embodiment.

Whereas the modification in FIG. 7 is formed of four frame memories 54a, 54b, 54c and 54d, this modification is formed of three frame memories.

A video signal having had $\gamma$ correction by the $\gamma$-correcting circuit 39 is branched, one branch is input into the A/D converter 41 and the other branch is connected to switches 121, 122 and 123. The A/D converter 41 digitalizes the video signals and writes them respectively into the R frame memory 58a, G frame memory 58b and B frame memory 58c. The outputs of the respective frame memories 58a, 58b and 58c are analogized respectively by D/A converters and are then input respectively into the above mentioned switches 121, 122 and 123. These switches 121, 122 and 123 have respectively two input terminals 121a and 121b, 122a and 122b and 123a and 123b and respectively one output terminal 121c, 122c and 123c. The video signals from the γ-correcting circuit 39 are input into the input terminals 121a, 122a and 123a. The color signals from the D/A converters 44 are input into the input terminals 121b, 122b and 123c. These switches 121, 122 and 123 are respectively separately controlled in switching by a control signal from the control circuit 46.

The output terminals 121c and 123c of the switches 121 and 123 are connected to the input terminals 48a and 49a of the switches 48 and 49. The output terminal 122c of the switch 122 is connected to the input terminals 48b and 49b of the switching switches 48 and 49 and the monitor 6.

The other formations are the same as in FIG. 7 which is of the modification of the first embodiment.

The operation of this modification shall be explained by using FIG. 10.

From the γ-correcting circuit 39, the γ-corrected video signals are input into the switches 121, 122 and 123 and A/D converter 41 by sequential signals of R, G and B as in FIG. 10(b). Here, for example, when the color signal $R_1$ is output from the γ-correcting circuit 39, this color signal $R_1$ will be input into the A/D converter 41 and the input terminals 121a, 122b and 123a of the switches 121, 122 and 123. In the A/D converter 41, the color signal $R_1$ is digitalized and is output to the memory part 58 in which a writing signal is input into the R frame memory 58a from the control circuit 46 and the color signal $R_1$ is written into the R frame memory 58a by this writing signal. Simultaneously with outputting the writing signal, the control circuit 46 outputs a reading signal to the G frame memory 58g and B frame memory 58c and reads color signals G and B out of the G frame memory 58b and B frame memory 58c.

By the way, in FIGS. 10(b), (c), (d) and (e), the circle (○) mark represents that the frame memory is in the reading-out state.

The read-out color signals G and B are analogized by the D/A converters 44 and are then input into the input terminals 122c and 123c of the switches 122 and 123.

On the other hand, the color signal $R_1$ written into the R frame memory 58a is simultaneously input into the input terminals 121a, 122a and 123a of the switches 122, 123 and 123 into which the control circuit 46 inputs a control signal to control the switching. The control circuit 46 outputs a control signal to receive the signal from the γ-correcting circuit 39 in the switches 121, 122 and 123 connected to the frame memory to which the writing signal is output and not to receive the signals from the frame memories 58a, 58b and 58c in the switches 121, 122 and 123 connected to the frame memory to which the reading signal is output. That is to say, in the state in FIG. 9, as the writing is made into the R frame memory 58a, the switch 121 connected to this R frame memory 58a is switched to the input terminal 121a side and the switches 122 and 123 connected to the G frame memory 58b and B frame memory 58c out of which the reading is being made are switched to the input terminal 122b and 123b sides.

The color signal $R_1$ which is the color signal being thus written in and the color signals $G_0$ and $B_0$ read out of the G frame memory 58b and B frame memory 58c are output to the monitor 6.

Then, the color signal $G_1$ is output out of the γ-correcting circuit 39 and is output to the memory part 58 through the A/D converter 41. In this memory part 58, the writing signal is output to the G frame memory 58 from the control circuit 46 and the color signal G1 is written into the G frame memory 58b. In the other frame memories 58a and 58c, the reading signals from the control circuit 46a are input and the color signals $R_1$ and $B_0$ are read out.

By the control signal from the control circuit 46, the switch 122 is switched to the input terminal 122a side and the other switches 121 and 123 are switched to the input terminal 121b and 123b sides.

The color signal $G_1$ which is the color signal being thus written in and the color signals $R_1$ and $B_0$ read out of the R frame memory 58a and B frame memory 58c are output to the monitor 6.

Then this operation is sequentially repeated to output the color signals to the monitor 6 which displays a color moving picture which is an ordinary observing picture image.

In the control circuit 46, the same as in FIG. 7 which is of the modification of the first embodiment, when the writing of the color signals into the frame memories end, as in FIG. 10(f), the one-frame memory writing-in end signal will be output to the synchronizing circuit 57.

When the body outside light observing switch 47 is switched on to confirm the position of the tip part 11, the on-signal shown in this FIG. 10(g) will be input into the synchronizing circuit 57 which outputs a black and white/color display switching signal as in FIG. 10(h) as synchronized with the rise of the one-frame memory writing-in end signal just after this on-signal. This black and white/color display switching signal is input into the switches 48 and 49 and is switched as described in the first embodiment so that a picture image of a black and white moving picture by a monochrome which is a picture image different from the normal observing picture image may be displayed in the monitor 6.

When the confirmation of the tip part 11 ends and the on-signal is again input from the body outside light observing switch 47, the synchronizing circuit 57 will switch off the black and white/color display switching signal which is on as synchronized with the rise of the one-frame memory writing-in end signal just after this on-signal. By this off-signal, the switches 48 and 49 are switched and the moving picture of the color picture image which is the ordinary observing picture image is again displayed in th monitor 6.

The other formations and effects are the same as of the first embodiment.

Figure 11:
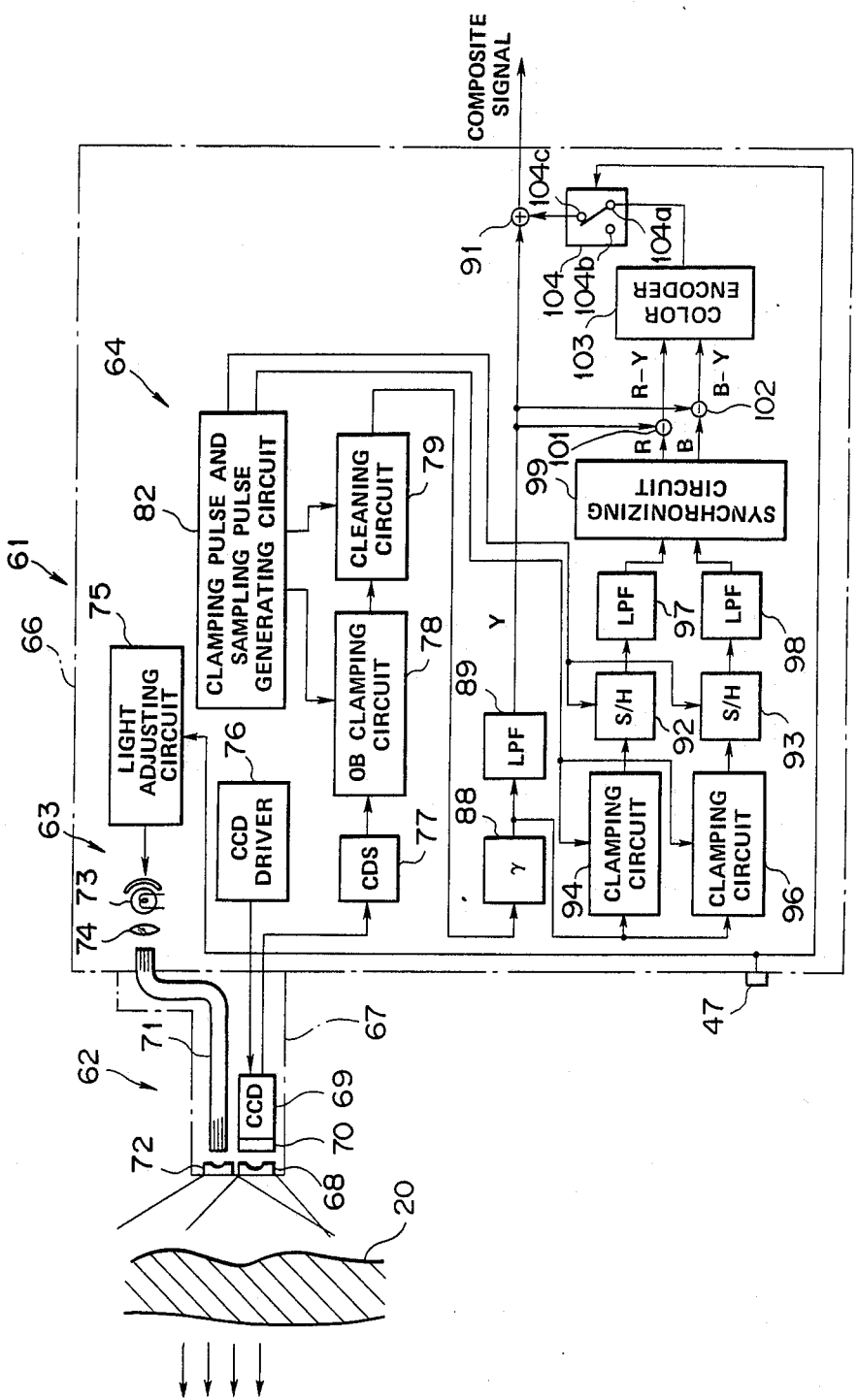

FIGS. 11 and 12 show the second embodiment of the present invention.

This embodiment is an electronic endoscope apparatus in which the present invention is applied to a simultaneous type imaging system.

An endoscope apparatus 61 comprises an electronic endoscope 62 in which an imaging means is incorporated and a control apparatus containing a light source part 63 for feeding an illuminating light to this electronic endoscope 62 and a signal processing part 64 for converting the signal imaged by this electronic endoscope 62 to a video signal which can be displayed in a displaying apparatus.

In the above mentioned electronic endoscope 62, an elongate insertable part 67 is formed so as to be easy to insert into a body cavity and, on the tip surface side of this insertable part 67, an objective lens 68 and CCD 69 are arranged and an imaging means is incorporated. By the way, a color mosaic filter not illustrated provided with filters in the form of a mosaic transmitting the respective colors, for example, of red (R), green (G) and blue (B) is fixed on the imaging surface of the CCD 69.

A light guide 71 for transmitting an illuminating light is inserted through the above mentioned insertable part 67, transmits the illuminating light fed from the light source 63 and emits it from the tip surface. This emitted illuminating light illuminates the object side through a light distributing lens 72.

The light source part 63 feeding the illuminating light is provided on the hand base side end surface of the above mentioned light guide 71 and is provided with a light source lamp 73 and a condenser lens 74 for condensing a white light emitted from this light source lamp 73. By the way, the light source lamp 73 is adjusted in the light amount by a light adjusting circuit 75.

The image of the object illuminated by the above mentioned illuminating light is formed on the imaging surface of the CCD 69 by the objective lens 68 and is separated into colors by a color mosaic filter not illustrated. An optical low pass filter (LPF) 70 is provided on the imaging surface of the CCD 69 so as to prevent mostly a color moire from being caused by the interference of the above mentioned color mosaic filter and the spatial frequency of the object image.

A signal photoelectrically converted by the application of driving pulses for transferring and reading the object image formed on the above mentioned CCD 69 out of the CCD driving circuit 76 is read out.

The output signal of the CCD 69 is input into a correlated double sampling circuit (which shall be abbreviated as a CDS circuit hereinafter) 77 forming the signal processing part 64. In this CDS circuit 77, the feedthrough part and signal component of the CCD output signal are sample-held and differentiated and such noise as mostly of 1/f generated from the CCD 69 is removed to obtain a video signal of a base band.

The output signal of the CDS circuit 77 is input into an optical black clamping circuit (which shall be abbreviated as an OB clamping circuit hereinafter) 78 and an optical black period (which shall be abbreviated as an OB period hereinafter) which is a black reference level of the CCD 69 output is direct current-clamped by clamping pulses generated from a clamping pulse and sampling pulse generating circuit 82 to prevent a black level fluctuation by the increase and decrease of a dark current of the CCD 69. The output signal of this OB clamping circuit 78 is input into a cleaning circuit 79 and the OB period and H blanking period are cleaned. The output of the cleaning circuit 79 is input into a γ-correcting circuit 88 which converts the γ characteristic $\gamma = 1$ of the output video signal of the CCD 69 to be $\gamma = 0.45$. The output of this γ-correcting circuit 88 is input into the low pass filter (LPF) 89, the color signal carrier component is removed and the luminance signal y is extracted and is input into the mixer 91.

On the other hand, the line-sequentially modulated color signal components are fixed in the direct current level as superimposed respectively on the luminance signal Y in the clamping circuits 94 and 96, the peaks of the carrier components modulated in the timing of the respective lines are sample-held in the sample holding circuits 92 and 93 and the base band components of the color signals are obtained through the low pass filters (LPF's) 97 and 98. These signals are line-sequential color signals R and B and are converted to color signals R and B synchronized by a synchronizing circuit 99 obtaining a delay time by one line for example, a CCD type delaying circuit of 1 H. The obtained color signals R and B are converted to color difference signals R-Y/B-Y by operating circuits 101 and 102 with the luminance signal Y and are subjected to a rectangular two-phase conversion by a subcarrier by a color encoder circuit 103 to obtain one added chrominance signal (which shall be abbreviated as a chroma signal hereinafter). This chroma signal will become a composite video signal when mixed with the luminance signal Y by the above mentioned mixer 91 through one input terminal 104 of an output switch 104 of two inputs and one output as a selecting means. By the way, in the mixer 91, by a synchronized signal generator not illustrated, a composite video signal is fed and added. The other input terminal 104b of the above mentioned switch 107 of two inputs and one output is open or connected to the GND.

The above mentioned composite video signal is output to a monitor not illustrated and displays the observed part with a picture image. This picture image is a color moving picture which is of an ordinary observing picture image.

The above mentioned switch 104 of two inputs and one output is connected so that a signal may be input from the body outside light observing switch 47, selects the input terminal 104b side with an on-signal of the body outside light observing switch 47 and selects the input terminal 104a with an off-signal. Further, the body outside light observing switch 47 is connected to the above mentioned light adjusting circuit 75 so as to increase the light amount of the light source lamp 73 when the on-signal is input from the switch 47.

The operation of the electronic endoscope apparatus 61 formed as in the above shall be explained.

The operator inserts the insertable part 67 of the electronic endoscope 62 into a body cavity. The interior of the body cavity is illuminated by an illuminating light emitted by the light source part 63 and the image of the observed part is formed on the imaging surface of the CCD 69. The image of the CCD 69 is read out by the CCD driver 76 and is processed to be a signal as predetermined by the circuits after the CDS circuit 77. The color difference signals R-Y and B-Y obtained by the signal processing are made a chroma signal by the color encoder circuit 103 and the chroma signal is input into the input terminal 104a of the switch 104 of two inputs and one output. In the switch 104 of two inputs and one output, in case no on-signal is input from the body outside light observing switch 47, the input terminal 104a and output terminal 104c are connected with each other and the input chroma signal will be input into the mixer 91. In the mixer 91, a composite video signal is produced by the luminance signal Y and chroma signal and a picture image of a color moving picture which is a normal observing picture image is displayed in a monitor not illustrated.

During the inserting operation, in the case of confirming the position of the tip part 11, the operator switches on the body outside light observing switch 47 provided in the control apparatus 66. The on-signal shown in FIG. 12(b) is input into the light adjusting circuit 75 and increases the light amount emitted by the light source lamp 73. This increased illuminating light is emitted into the body cavity through the light guide 71 and light distributing lens 72. A part of the illuminating light emitted into the body cavity is transmitted through a living body tissue and is emitted out of the body By sighting this transmitted light, the operator can confirm the position of the tip part of the electronic endoscope 62.

On the other hand, the reflected light from the observed part forms an image on the CCD 69 through the objective lens 68, optical LPF 70 and color mosaic filter not illustrated. As the light source lamp 73 has increased the light amount, the light amount entering this CCD 69 is larger than a proper exposure amount. Therefore, by the fundamental principle of the mosaic system in which the luminance signal Y is obtained as a carrier signal of a modulated color signal, the color signal is likely to be saturated and the obtained picture image has a color omission and is ugly. The on-signal output in the light adjusting circuit 75 here is input also into the switch 104 of two inputs and one output and selects the input terminal 104b side open or connected to the GND. Thereby, the chroma signal is not input into the mixer 91 and only the luminance signal Y is output to the monitor. The picture image displayed in the monitor is an unsaturated normal black and white moving picture different from the ordinary observing picture image.

Then, in case the operator ends the confirmation of the tip position by the body outside light transmitting light, the body outside light observing switch 47 will be again switched off. This off-signal is input into the light adjusting circuit 75 and the light amount of the light source lamp 73 is reduced so that the illuminating light amount may be adapted to the color picture image of the normal observing color picture image. At the same time, the off-signal is input also into the output switch 104 of two inputs and one output, the input terminal 104a is selected, the chroma signal is input into the mixer 91 and a picture image of a color moving picture of an ordinary observing picture image is displayed. By the way, such time setting circuit as is shown in FIG. 4 may be provided instead of inputting on-off-signals from the body outside light observing switch 47.

The embodiment shall be explained more in detail by using FIG. 12. When such on-signal as in FIG. 12(b) is input from the body outside light observing switch 47, as synchronized with this on-signal, the switch 104 will select the input terminal 104b side and the monitor picture image will display a moving picture of a black and white picture image which is a picture image different from the normal observing picture image. When the body outside light observing switch 47 is pushed again and an on-signal is input, as synchronized with this on-signal, the switch 104 will select the output terminal 104c side and the monitor picture image will be a moving picture of a color picture image which is an ordinary observing picture image.

As in the above, according to this embodiment, the light amount for confirming the endoscope tip position is increased, even if the color signal component of the output signal of the CCD 69 is saturated, a picture image of a clear black and white moving picture will be able to be displayed in the observing monitor and an electronic endoscope apparatus of improved safety and operatability can be provided. This embodiment is of a mosaic type electronic endoscope but can be easily applied to the frame sequential type described in the first embodiment.

Figure 13:
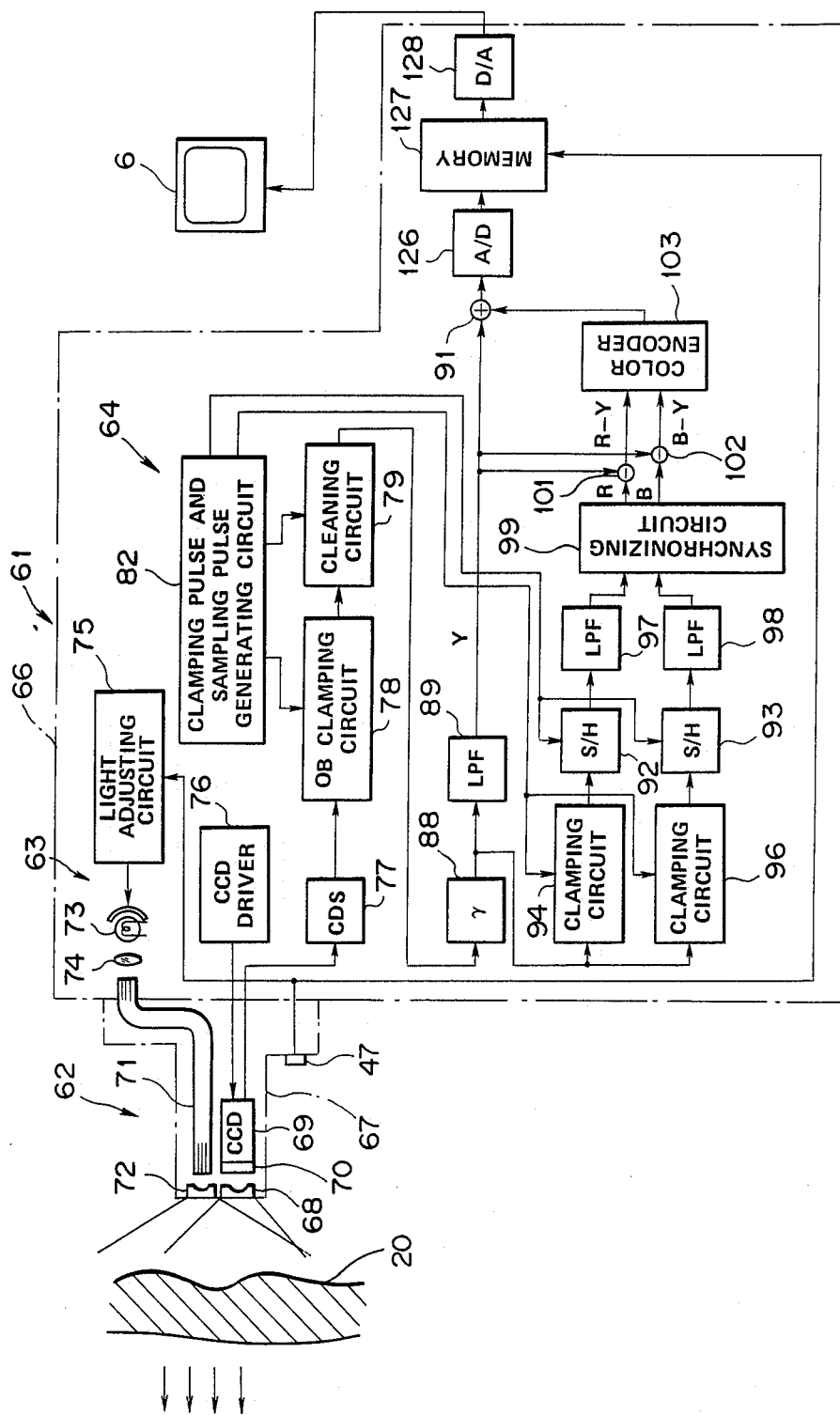
FIGS. 13 and 14 relate to the third embodiment of the present invention.
Figure 14:
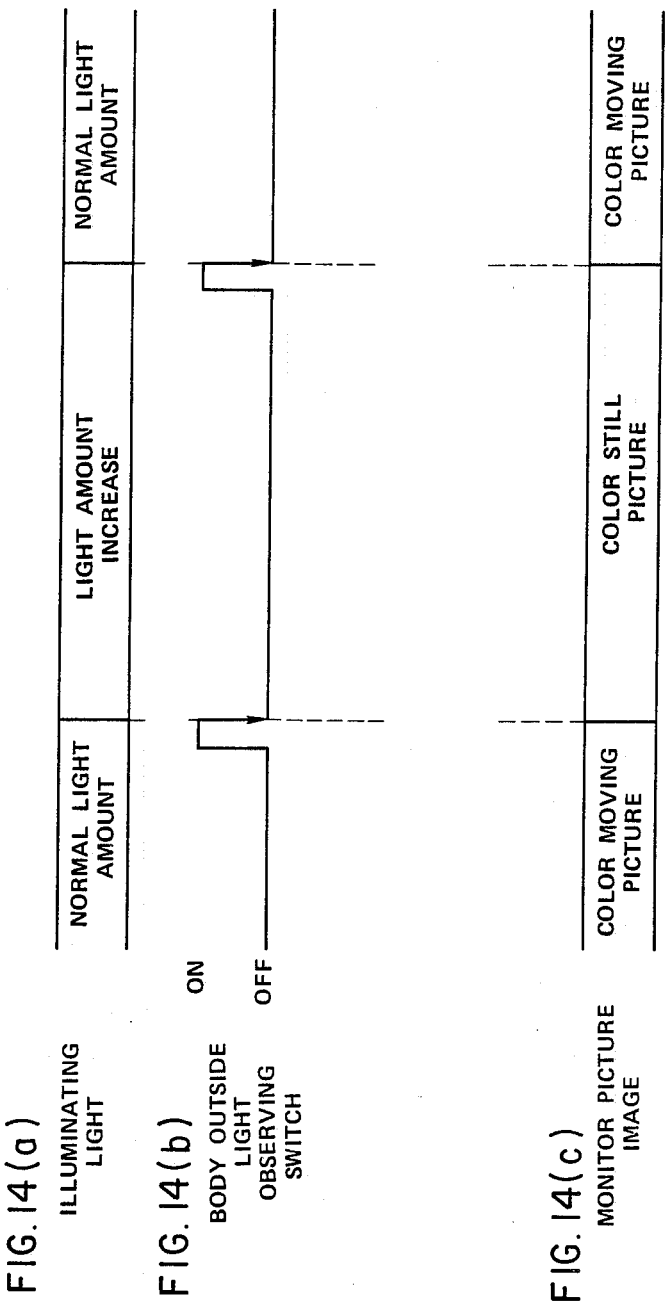

FIGS. 13 and 14 show the third embodiment of the present invention.

Whereas a black and white moving picture is displayed in the monitor 6 in the second embodiment, a color still picture as a picture image different from the normal observing picture image is displayed in the monitor 6 in this embodiment.

The formation of this embodiment is substantially the same as of the second embodiment but the switch 104 is omitted and an A/D converter 126, memory 127 and D/A converter 128 are provided after the mixer 91.

The explanation shall be made from the mixer 91. A composite signal mixed by the mixer 91 is digitalized by the A/D converter 126 and is input into the memory 127 by which the input signal is once written in, is immediately read out and is output to the D/A converter 128. The output of this D/A converter 128 is delivered to the monitor 6 which displays a moving picture of a color picture image which is a normal observing picture image.

The body outside light observing switch 47 is switched on to confirm the position of the tip part 11. As synchronized with the on-signal shown in FIG. 14(b), the memory 127 inhibits writing in the signal, repeats the signal already written in and outputs it to the monitor 6 which displays a color still picture image which is a picture image different from the normal observing picture image.

When the position confirmation ends and the on-signal is again input from the body outside light observing switch 47, the memory 127 will release the inhibitiion of writing in and will write in and read out the signal. Thereby, the monitor 6 displays a color moving picture which is an ordinary observing picture image The other formations and effects are the same as of the second embodiment.

FIGS. 15 and 16 show the fourth embodiment of the present invention.

In the above described first to third embodiments, either of a clear black and white picture image and color still picture is obtained as a picture image different from the normal observing picture image. However, with only the black and white picture image or color still picture, the information amount may be short in some case. In this embodiment, the information amount in this function can be displayed to the maximum.

This embodiment has a television-in-television mode which can simultaneously display in the monitor 6 parent and son pictures as picture images different from the normal observing picture image.

FIG. 15 shows the formation after the A/D converter 41. The circuits not illustrated are the same as in FIG. 2 and shall not be explained here.

In FIG. 15, in the case of observing a picture image of a color moving picture of an ordinary observing picture image, the video information digitalized by the A/D converter 41 is written into a still picture memory 106 and moving picture memory 107. The video information written into the moving picture memory 107 is read out to a memory controller 108 at a controlled timing and is input into the D/A converter 44 through a mixer 109. Among the color signals R, G and B analogized by the D/A converter 44, the R signal is input into the input terminal 48a of the output switching switch 48 of two inputs and one output and the B signal is input into the input terminal 49a of the output switch 49 of two inputs and one output. These input terminals 48a and 49a are connected respectively with the output terminals 48c and 49c. The color signals R and B are output to the monitor 6. On the other hand, the color signal G is branched, is input into the input terminals 48b and 49b of the output switches 48 and 49 of two inputs and one output and is output to the monitor 6 in which the color signals R, G and B are input and a color moving picture of the normal observing picture image is displayed.

In the case of confirming the position of the endoscope tip, the body outside light observing switch 47 is switched on. The on-signal is input into the above mentioned memory controller 108, delaying circuit 111 and timing generating circuit 112. The memory controller 108 controls the still picture memory 106, inhibits writing in the video information and repeatedly outputs to the mixer 109 the video information just before the writing in is inhibited. The moving picture memory 107 has the reading-out timing and reading-out address controlled by the memory controller and the information is read out so as to be of the size and picture displaying position of the son picture 114 in FIG. 16(a) and is input into the mixer 109. The mixer 109 mixes the video information of the still picture and the video information of the moving picture and outputs them to the D/A converter 44. The color signals R and B which are output signals of the D/A converter 44 are output to the output switches 48 and 49 and the color signal G is output directly to the monitor 6. The switches 48 and 49 of two inputs and one output have the switching timing controlled by the above mentioned timing generator 112. In case the output of the D/A converter 44 is the information of a moving picture, the timing generator 112 will not output a timing signal as shown in FIG. 16(b) and the input terminal 48b and 49b sides of the output switches 48 and 49 will be selected. As in FIG. 16(b), at the timing of the time when the video information of a still picture is output from the D/A converter 44, a timing signal is output to the switches 48 and 49 of two inputs and one output. By this timing signal, the input terminal 48a and 49a sides of the switches 48 and 49 of two inputs and one output are selected and the color signals R, G and B which are the video information of the still picture are output to the monitor 6. The signal output to the monitor 6 as the moving picture information is a monochromatic color signal G which is output as color signals R, G and B to obtain a clear black and white moving picture. The signal output to the monitor 6 as the video information of a still picture is color signals R, G and B to obtain a still picture of a color picture image. Thereby, in the monitor 6, a color still picture is displayed for the parent picture 113 which is a picture image different from the normal observing picture image and a black and white moving picture is displayed for the son picture 114.

On the other hand, after the end of writing the video information into the still picture memory 106, by the above mentioned delaying circuit 111, a control signal is output to the filter moving motor 31 and the rotary color filter 24 is retreated from the light path of the illuminating light.

When the confirmation of the endoscope tip position ends, the body outside light observing switch 47 will be switched off. This off-signal is input into the memory controller 108 to release the inhibition of writing into the still picture memory 106 and is further input also into the timing generator 112 to stop the generation of the timing signal. As no timing signal is input, the input terminal 48a and 49a sides of the switches 48 and 49 of two inputs and one output are selected and the color signals R, G and B are output to the monitor 6 to display a moving picture of a color picture image which is a normal observing picture image.

As mentioned above, according to this embodiment, the maximum video information can be taken out of the obtained video data and an electronic endoscope apparatus high in the safety and operatability can be provided.

The body outside light observing switch 47 is not limited to be provided in the signal processing apparatus body but may be provided in either of the light source apparatus and signal processing apparatus in case they are separate from each other. It is needless to say that, if it is provided on the operating part in the rear of the endoscope, the operatability will be improved.

Figure 17:
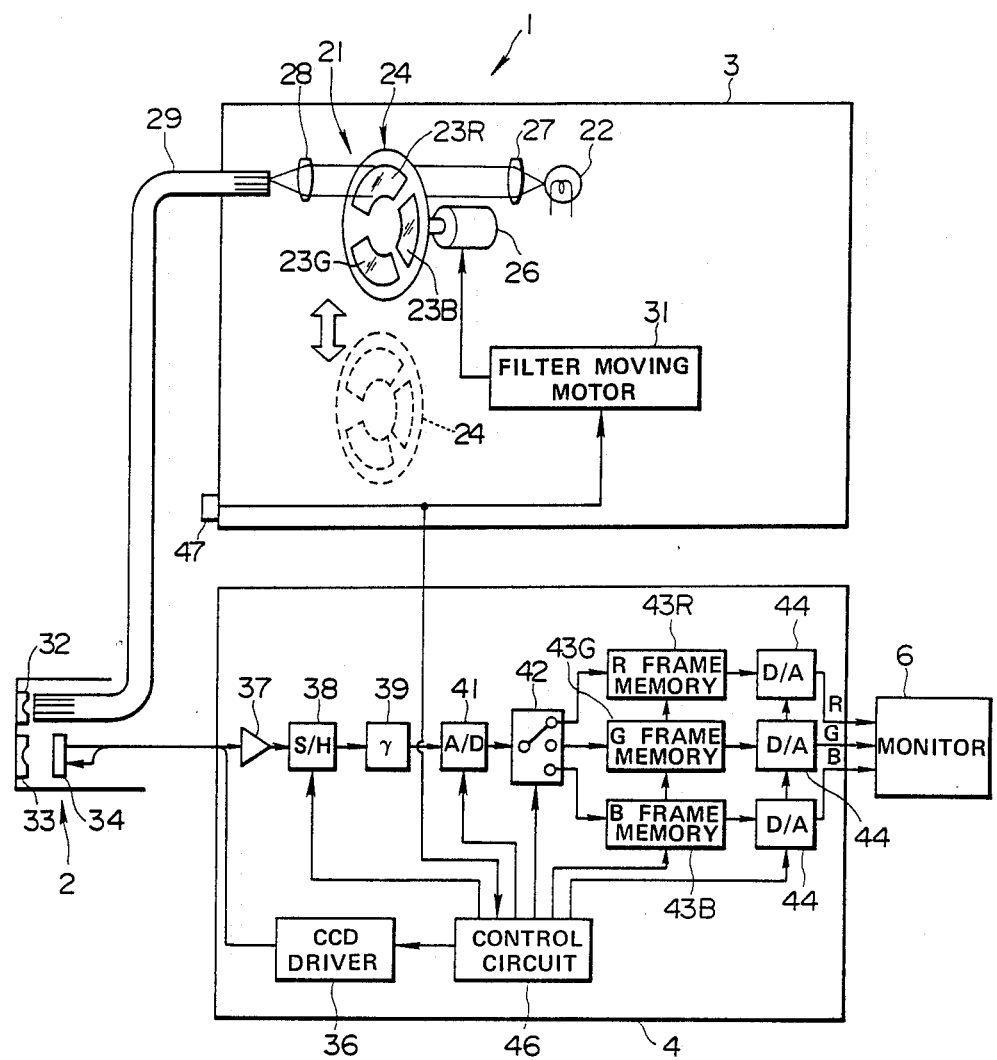
FIGS. 17 and 18 relate to the fifth embodiment of the present invention.
Figure 18:
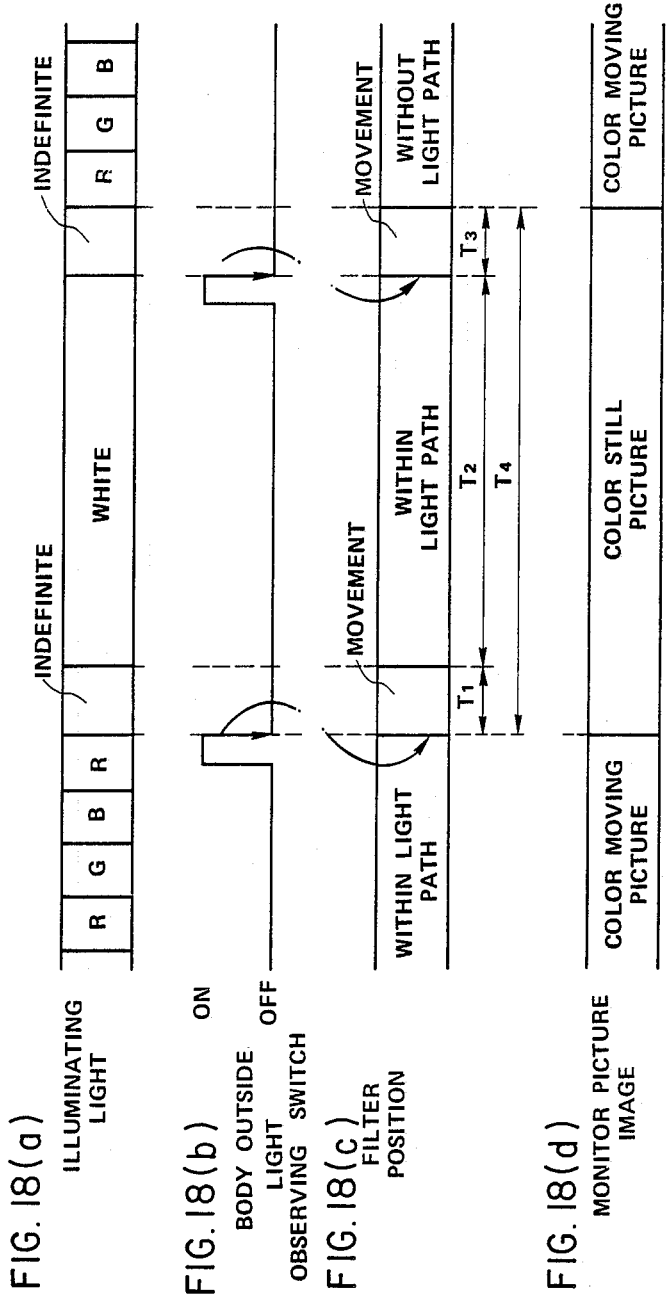

FIGS. 17 and 18 show the fifth embodiment of the present invention.

In the case of confirming the position of the tip part, in the first embodiment, a moving picture of a black and white picture image is displayed in the monitor 6 as a picture image different from the normal observing picture image, whereas, in this embodiment, a color still picture is displayed.

The formation of this embodiment is the formation of the first embodiment less the switches 48 and 49. The other formations are the same as of the first embodiment.

The formation after the A/D converter 41 shall be explained.

The electric signal converted to a digital signal by the A/D converter 41 is repeated as synchronized with a color frame sequential illuminating light by the multiplexer 42 and is sequentially written into the R frame memory 43R, G frame memory 43G and B frame memory 43B corresponding to the respective colors of red, green and blue. The signals are simultaneously read out of the respective frame memories 43R, 43G and 43B in the horizontal direction at a speed matching the monitor 6 and are respectively converted to analogue signals by the D/A converter 44 to be three primary color signals of R, G and B. These three primary color signals are input into the monitor 6 so that a color picture image of the observed part may be displayed as an ordinary observing picture image.

The on/off-signal is input into the above mentioned control circuit 46 from the body outside light observing switch 47 provided in the light source apparatus 3 together with the above mentioned filter moving motor 31. When the on-signal is input, the control circuit 46 will inhibit writing into the respective frame memories 43R, 43G and 43B and the picture image displayed in the monitor 6 will be a color still picture image which is a picture image different from the normal observing picture image. By the on-signal, the filter moving motor 31 will retreat the rotary color filter 24 from the light path connecting the light source lamp 22 and the entrance end surface of the light guide 29. Further, when the body outside light observing switch 47 is again switched on, the filter moving motor will insert the rotary color filter 24 into the light path and the control circuit 46 will release the inhibition of writing into the respective frame memories 43R, 43G and 43B. When the inhibition of writing into the respective frame memories 43R, 43G and 43B is released, the picture in the monitor 6 will be a color moving picture which is a normal observing picture image.

The operation of the electronic endoscope apparatus 1 formed as in the above shall be explained by using the timing chart diagram in FIG. 18.

The operator inserts the insertable part 7 of the endoscope 2 into a body cavity. The illuminating light emitted by the light source apparatus 3 is sequentially separated into respective color lights of R (red), G (green) and B (blue) as in FIG. 18(a) and is fed to the light guide 29.

During the inserting operation, in case the position of the tip part 11 is to be confirmed, the operator switches on the body outside light observing switch 47 provided in the light source apparatus 3. By this on-signal, the filter moving motor 31 will start driving and the rotary color filter 24 will begin to retreat from the light path as in FIG. 18(c). In this moving period $T_1$, the illuminating light is indefinite. At the time when the movement of the rotary color filter is completed, the illuminating light will become a white light increased in brightness and it will be easy to confirm the position of the tip part 11 with the light transmitted from within the body. By the on-signal of the body outside observing switch 47, the control circuit 46 will inhibit writing into the respective frame memories 43R, 43G and 43B, the picture image in the monitor 6 will be made a color still picture image which is a picture image different from the normal observing picture image and the color picture image just before the rotary color filter 24 moves will be displayed.

When the operator then ends the confirmation of the tip position with the transmitted light of the body outside light, the body outside light observing switch 47 will be again switched on. By this on-signal, the rotary color filter having retreated out of the light path will begin to move into the light path. After the end of the moving period $T_3$, the movement will end and, when the illuminating light changes to R (red), G (green) and B (blue) separated from the white light, the control circuit 46 will release the inhibition of writing into the respective frame memories 43R, 43G and 43B. The new video data of the observed part illuminated by the respective color lights of R (red), G (green) and B (blue) are sequentially written into the respective frame memories 43R, 43G and 43B and are simultaneously read out to display a color moving picture which is a normal observing picture image on the picture in the monitor 6.

In this embodiment, during the period $T_4$ which is the sum of the periods $T_1$ and $T_3$ when the rotary color filter 24 moves and the period $T_2$, when it is fixed out of the light path, the picture image is made a color still picture image. Therefore, during the operation of confirming the position of the tip part with the body outside light, no ugly picture image will be displayed.

Figure 19:
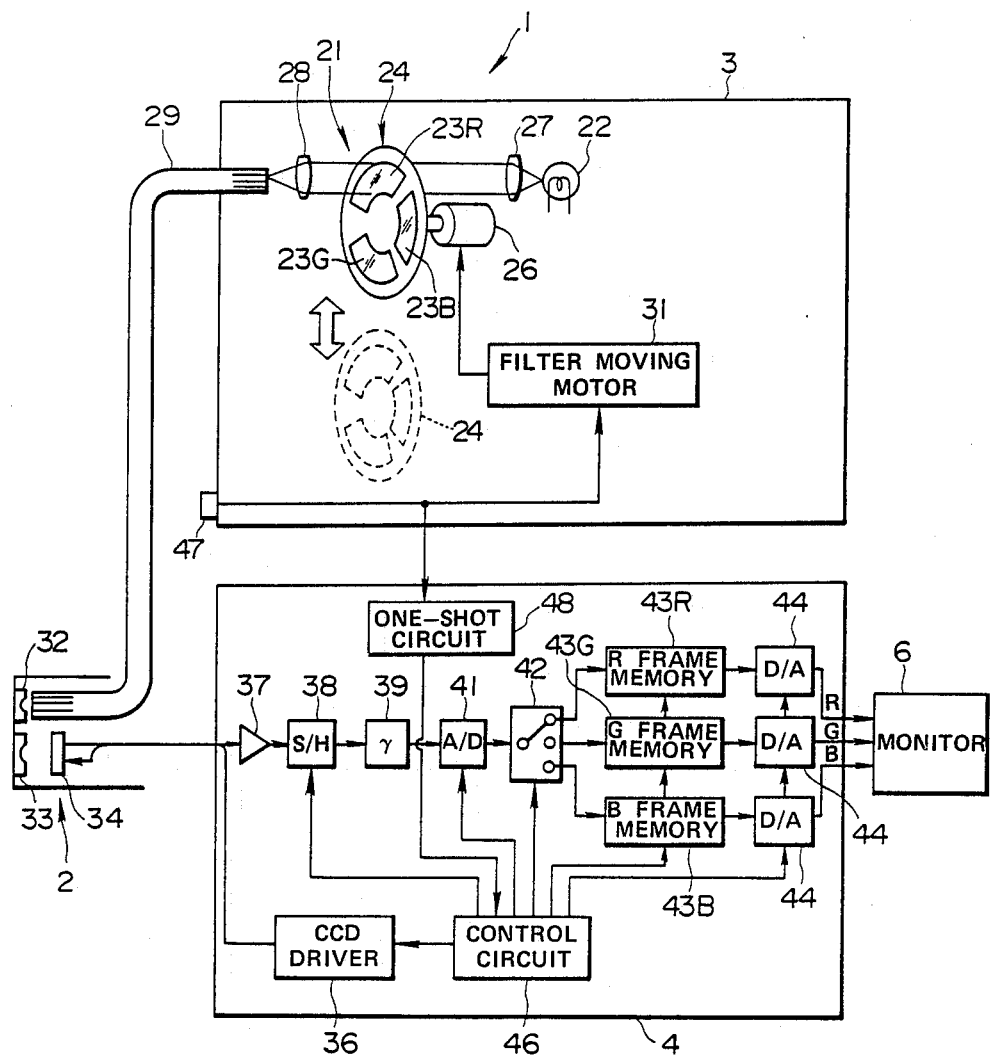
FIGS. 19 and 20 relate to the sixth embodiment of the present invention.
Figure 20:
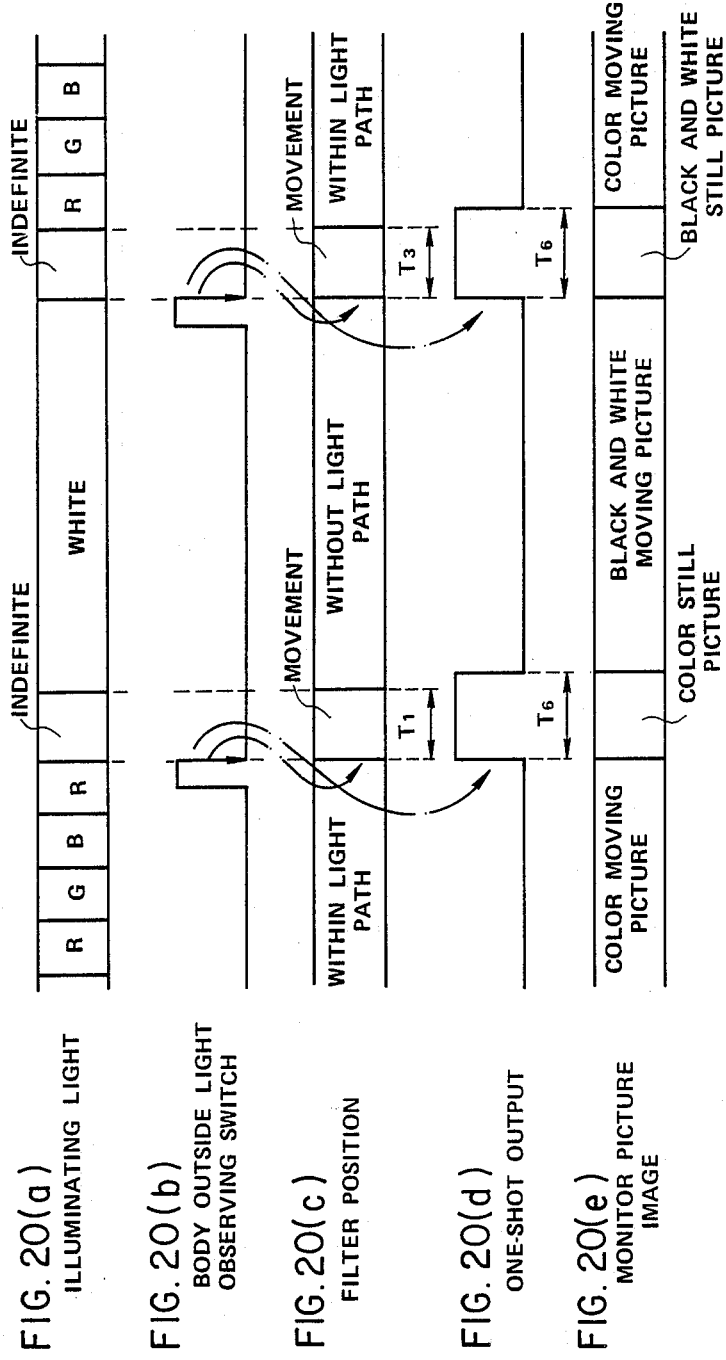

FIGS. 19 and 20 show the sixth embodiment of the present invention.

In this embodiment, the picture image is kept a still picture image during a period somewhat longer than the period when the rotary color filter 24 moves. By the way, in this embodiment, the formation and operation different from those of the first embodiment shall be described.

The body outside light observing switch 47 provided in the light source apparatus 3 can input on-signals into the filter moving motor 31 and the one-shot circuit 48 provided within the control circuit 4. When an on-signal is input, this one-shot circuit 48 will deliver a control signal to the control circuit 46.

In the timing chart view in FIG. 20, by the fall of the on-signal of the body outside light observing switch 47, the filter moving motor 31 will start driving and the color transmitting filters 23R, 23G and 23B of the rotary color filter 24 will retreat out of the light path after the moving period $T_1$. Further, by the fall of the on-signal, the one-shot circuit 48 will output one-shot pulses of an output pulse width $T_6$ somewhat longer than the filter moving period $T_1$. While these one-shot pulses are being input, the control circuit 46 will inhibit writing into the respective frame memories 43R, 43G and 43B to make the picture image in the monitor 6 a color still picture image. When the rotary color filter 24 retreats, after the period $T_6$, the control circuit 46 will release the inhibition of writing into the respective frame memories 43R, 43G and 43B. In this case, the illuminating light will be a white light and therefore the picture image in the monitor 6 will be a black and white moving picture which is a picture image different from the normal observing picture image.

When the confirmation of the tip position with the body outside transmitted light ends, the body outside light observing switch 47 will be switched on. By the fall of this on-signal, the rotary color filter 24 will begin to move to insert the color transmitting filters 23R, 23G and 23B into the light path and will end the insertion into the light path after the moving period $T_3$. Further, by the fall of this on-signal, the one-shot circuit 48 will again deliver pulses of an output pulse width $T_6$. While these pulses are being input, the control circuit 46 will inhibit writing into the respective frame memories 43R, 43G and 43B to make the picture image in the monitor 6 a black and white still picture image. After the moving period $T_3$, the rotary color filter 24 will begin to rotate and will sequentially emit the illluminating light separated into the respective color lights of R (red), G (green) and B (blue). After the period $T_6$, the control circuit 46 will release the inhibition of writing into the respective frame memories 43R, 43G and 43B and a color moving picture which is an ordinary observing picture image will be displayed in the monitor 6.

According to this embodiment, only in the periods ($T_1$ and $T_3$) when the rotary color filter 24 moves, the picture image will be made a still picture image. Therefore, even at the time of the body outside observation, though a black and white picture image, a moving picture will be able to be displayed in the monitor 6, the movement of the insertable part 7 will be able to be sighted and the operation will be safe. At the time of the movement of the rotary color filter, an ugly picture image will be able to be prevented from being output.

Figure 21:
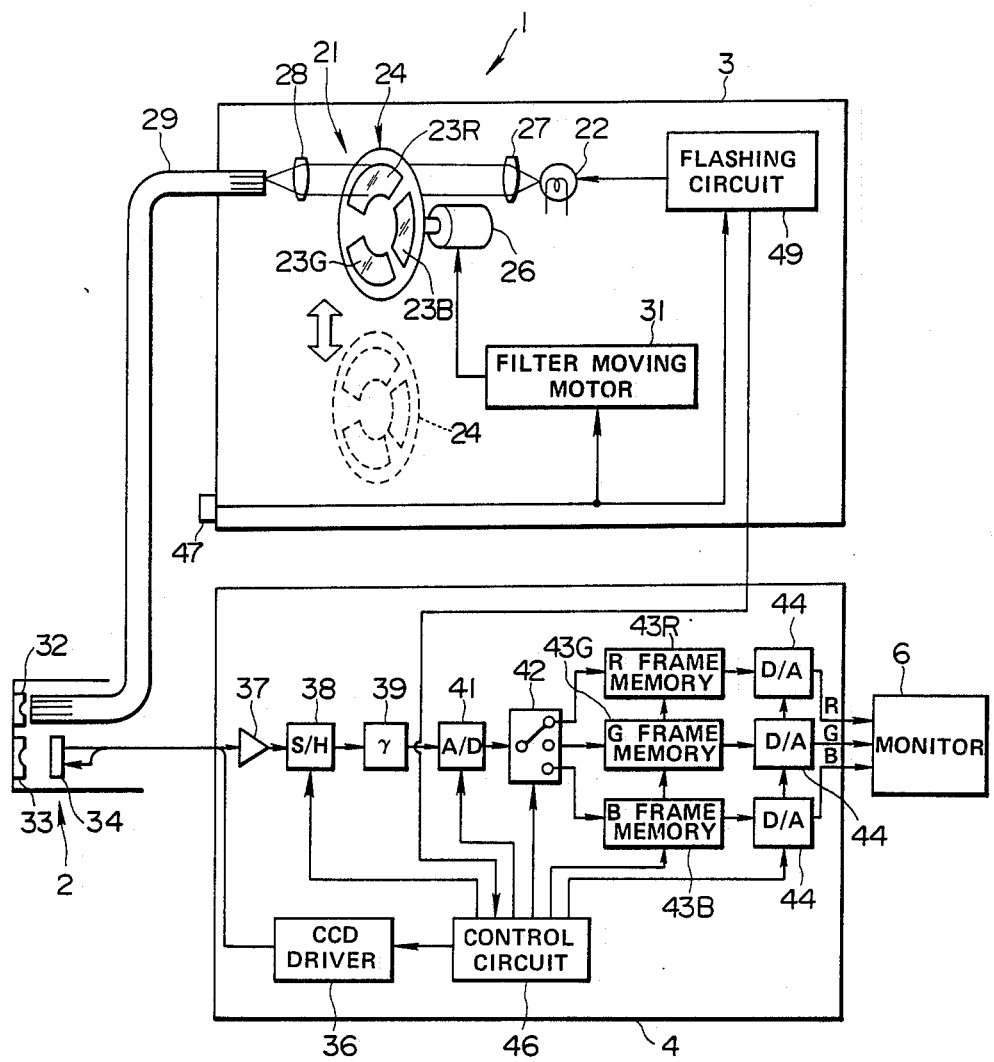

FIGS. 21 and 22 show the seventh embodiment of the present invention

In this embodiment, in the period when the rotary color filter 24 retreats from the light path, the light source lamp 22 will flash. By the way, in this embodiment, the formation and operation different from those of the first embodiment shall be described.

The body outside light observing switch 47 provided in the light source apparatus 3 can input on-signals into the filter moving motor 31 and flash circuit 49. When the on-signal is input, this flash circuit 49 will flash the light source lamp 22 and at the same time will deliver to the control circuit 46 a flash signal synchronized with this flash.

In the timing chart view in FIG. 22, by the on-signal of the body outside observing switch 47, the filter moving motor 31 will start driving and the color transmitting filters 23R, 23G and 23B of the rotary color filter will move out of the light path. After the moving period T₁, the color transmitting filters 23R, 23G and 23B will be retreated out of the light path. When this on-signal is input into the flash circuit 49, pulses of such pulse width T₅ as in FIG. 22(d) will be output to the control circuit 46 for a fixed pause period T₇ and the light amount of the light source lamp 22 will be increased synchronously with these pulses. During this pulse width T₅, the control circuit 46 will inhibit writing into the respective frame memories 43R, 43G and 43B and the picture image in the monitor 6 will be made a still picture image which is a picture image different from the ordinary observing picture image and, during the pause period T₇, the inhibition of writing into the respective frame memories 43R, 43G and 43B will be released. In case the writing-in inhibition is released, the illuminating light will be a white light and therefore the picture image in the monitor 6 will be a black and white moving picture which is a picture image different from the ordinary observing picture image. The flash circuit 49 will keep on delivering pulses until the on-signal is input from the body outside observing switch 47.

By the way, during the pause period T₇, the light source lamp 73 will output a light amount adapted to the normal color observation within the body but, during the pulse period T₅, it will output a light amount larger than the light amount adapted to the color observation. This larger light amount goes out of the body through the inner wall of the body cavity to be able to confirm the position of the tip part 11.

When the confirmation of the tip position with the body outside transmitted light ends, the body outside observing switch 47 will be switched on. By this on-signal, the rotary color filter 24 will begin to move to insert the color transmitting filters 23R, 23G and 23B into the light path and will end the insertion after the moving periot T₃. Further, by on-signal, the flash circuit 49 will stop the output of the next pulses and the control circuit 46 will release the inhibition of writing into the respective frame memories 43R, 43G and 43B. After the moving period T₃ the rotary color filter 24 will start the rotation and will sequentially emit the illuminating light separated into respective color lights of R (red), G (green) and B (blue) to display a color moving picture which is an ordinary observing picture image in the monitor 6. By the way, the flash period T₅ may be made longer than the moving period T₁ so that a still picture image may be made in the moving period T₁. Further, while the pulses are being input into the control circuuit 46, the picture image in the monitor 6 may be made a still picture image.

According to this embodiment, only during the flash period T₅, the picture image in the monitor 6 will be made a still picture image which is a picture image different from the normal observing picture image and therefore, in both periods when the rotary color filter 24 moves and at the time of the body outside light observation, a moving picture will be able to be observed, the safety will be higher and such ugly picture image as will be made really white by flashing will be able to be prevented.

Figure 23:
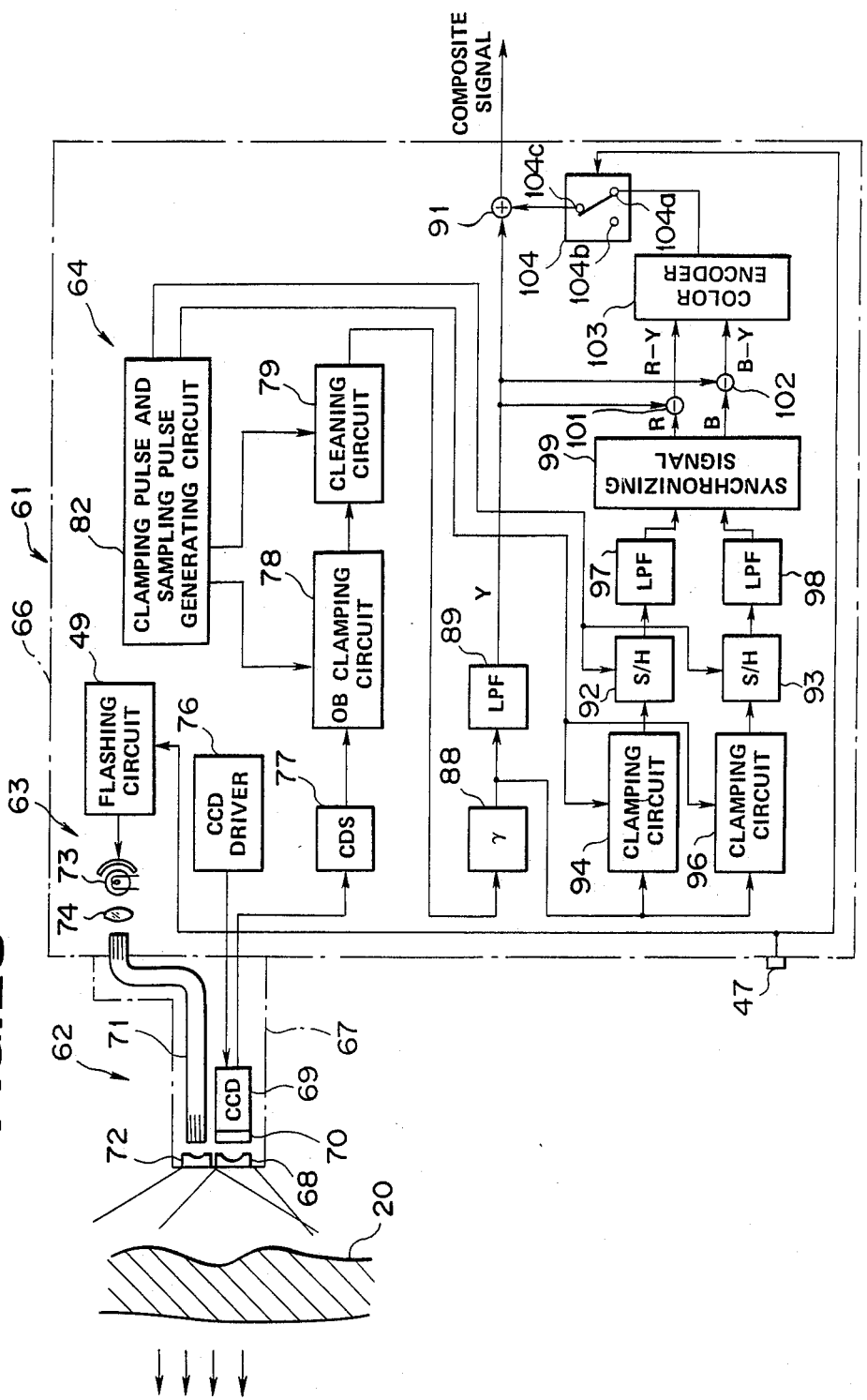
FIGS. 23 and 24 relate to the eighth embodiment of the present invention.
Figure 24:
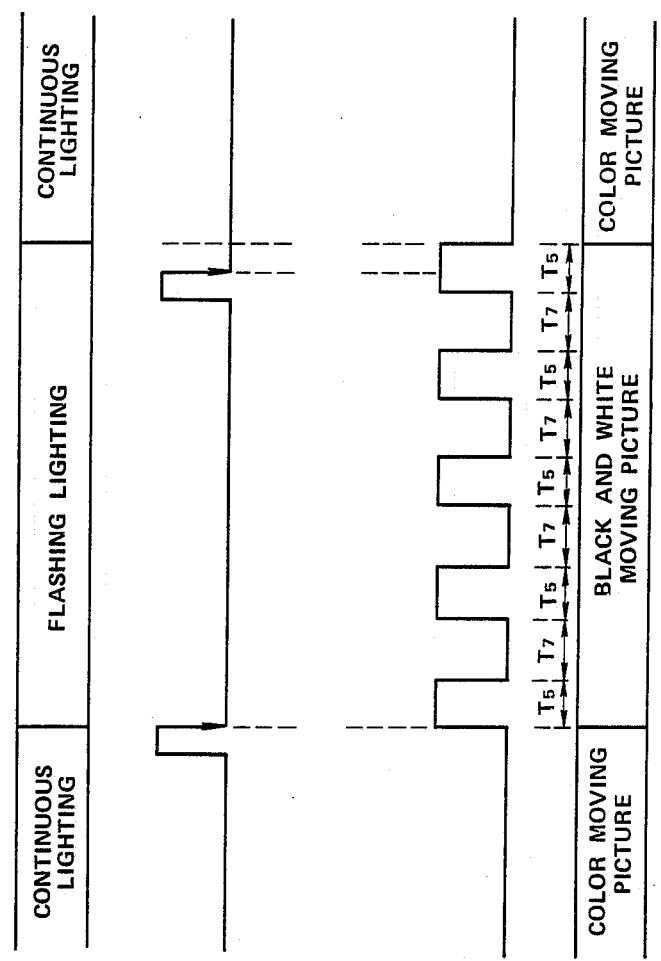
Figure 25:
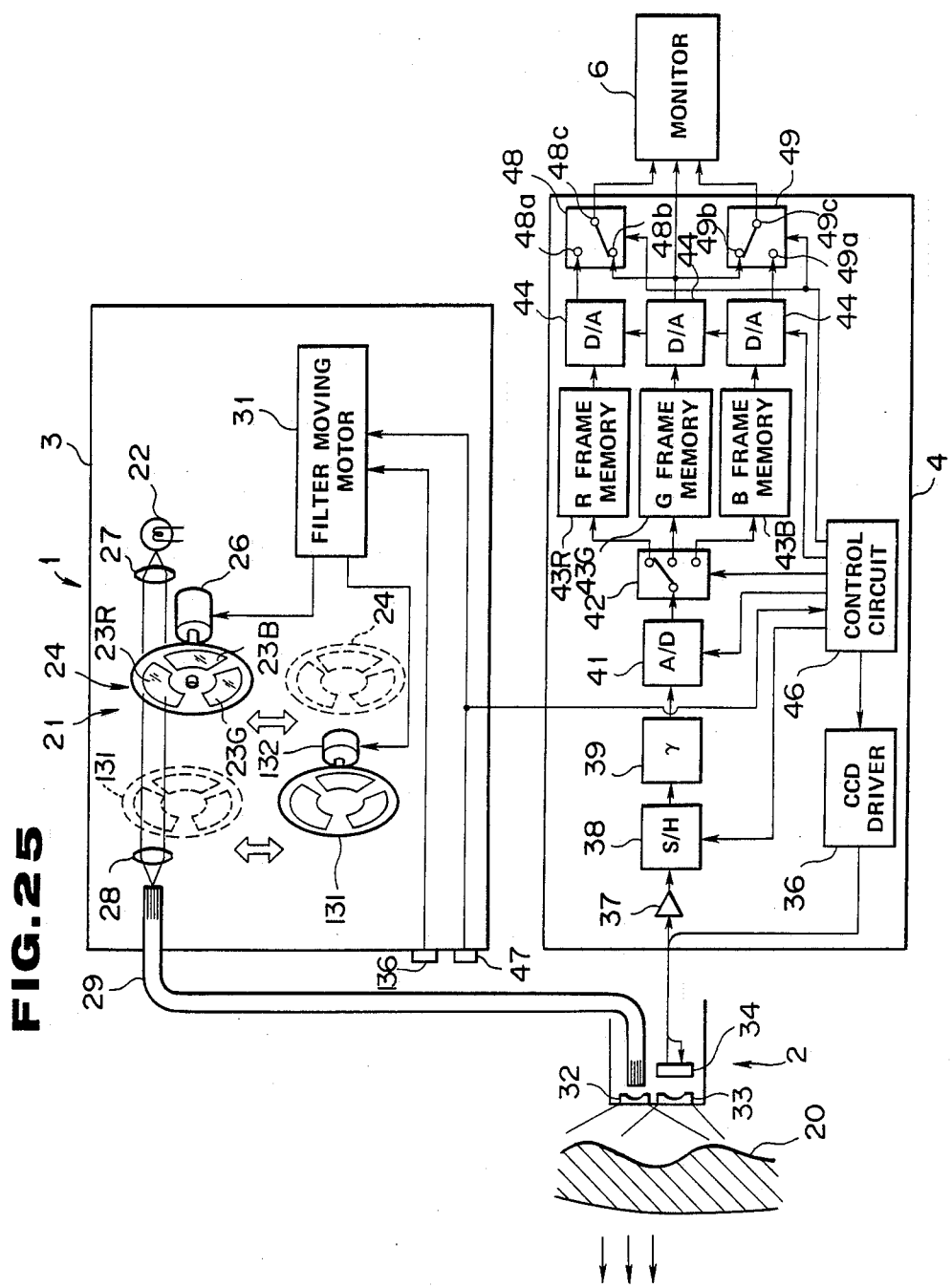
FIGS. 25 to 29 relate to the ninth embodiment of the present invention.

FIGS. 23 and 24 show the eighth embodiment of the present invention.

In this embodiment, the flash circuit 49 described in the seventh embodiment is provided instead of the light adjusting circuit 75 of the endoscope apparatus having the simultaneous type imaging system described in the second embodiment.

The formation of this embodiment is the same as of the second embodiment except that the light adjusting circuit 75 is replaced with the flash circuit 49 as mentioned above.

The operation of this embodiment shall be described.

In the case of confirming the position of the tip part 11, when the body outside light observing switch 47 is pushed, the on-signal from this switch 47 will be input into the flash circuit 49 and switch 104. When the on-signal is input, the flash circuit 49 will output to the light source lamp 73 pulses of such pulse width T₅ as in FIG. 24(c) for a fixed pause period T₇ to intermittently light the light source lamp 73. By the way, the light source lamp 73 will output a light amount adapted to the normal body interior color observation in the pause period T₇ but will output a light amount larger than the light amount adapted to the color observation in the pulse period T₅. This larger light amount can go out of the body through the inner wall of the body cavity and can be used to confirm the position of the tip part 11. The flash circuit 49 will keep on delivering pulses until the on-signal is input from the body outside light observing switch 47.

When the on-signal is input, the switch 104 will select the input terminal 104b side open or connected to the GND. Thereby, no chroma signal will be input into the mixer 91 but only the luminance signal Y will be output to the monitor in which a black and white moving picture which is a picture image different from the normal observing picture image will be displayed.

When the confirmation of the tip position with the body outside transmitted light ends, the body outside light observing switch 47 will be switched on. The on-signal is input into the flash circuit 49. When the on-signal is input, the flash circuit 49 will stop the output of pulses from the next time. As synchronized with the fall of the last pulse, the switch 104 will select the output terminal 104c side and will input a chroma signal into the mixer 91. Thereby, a color moving picture which is a normal observing picture image will be displayed in the monitor 6.

By the way, the switch 104 may be switched synchronously with the flash circuit 49 so that, as in FIG. 22(e), a color still picture may be displayed in the pulse period and a moving picture may be displayed in the pause period.

The other formations are the same as of the second embodiment.

FIGS. 25–29 relate to the ninth embodiment of the invention.

In this embodiment, the present invention is applied to a special light observing endoscope in which the observation can be made with not only the lights of red (R), green (G) and blue (B) but also other illuminating lights than visible lights.

The normal observing picture images in this embodiment include not only the picture images obtained with the illuminating lights of the visible lights of red (R), green (G) and blue (B) but also the picture images obtained with the other illuminating lights than the visible lights.

By the way, the formation of this embodiment is the same as of the first embodiment except that a special light observing rotary filter is provided.

The light source apparatus 3 is provided with not only a rotary color filter 24 for the visible light observation but also a special light rotary color filter 131 for the special light observation. This special light rotary color filter 131 is rotated and driven by a motor 132 and is removably inserted into the illuminating light path by the filter moving motor 31.

Figure 26:
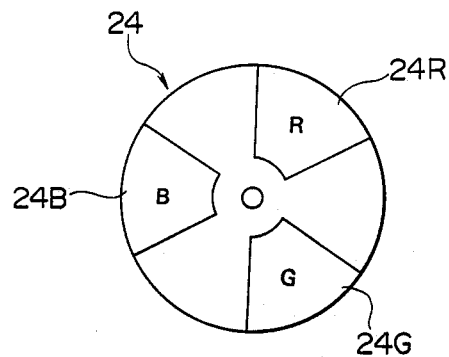
Figure 28:
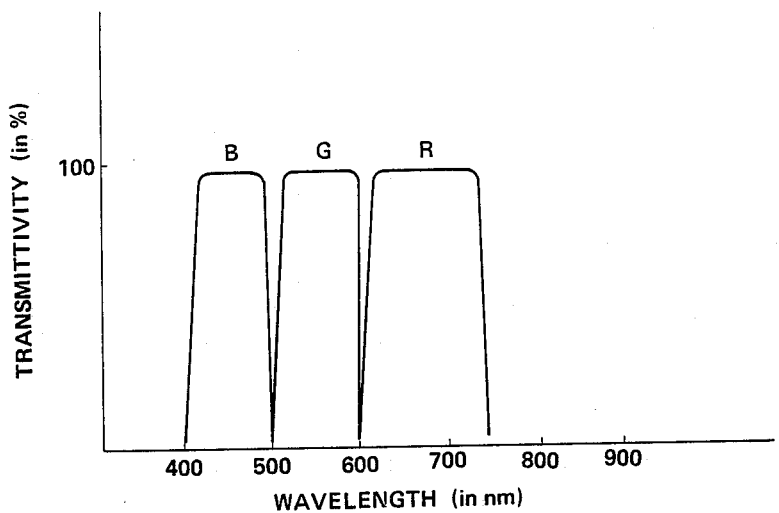

As shown in FIG. 28, in the above mentioned rotary color filter 24 for the visible light observation, filters 24R, 24G and 24B transmitting the lights of the respective wavelength regions of R, G and B are arranged in the peripheral direction as shown in FIG. 26.

Figure 27:
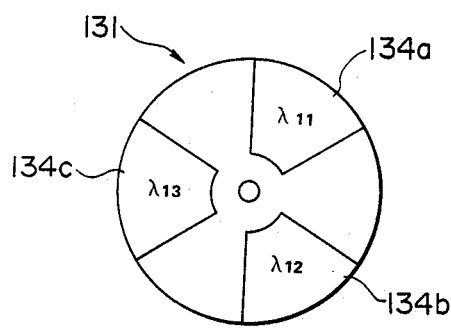
Figure 29:
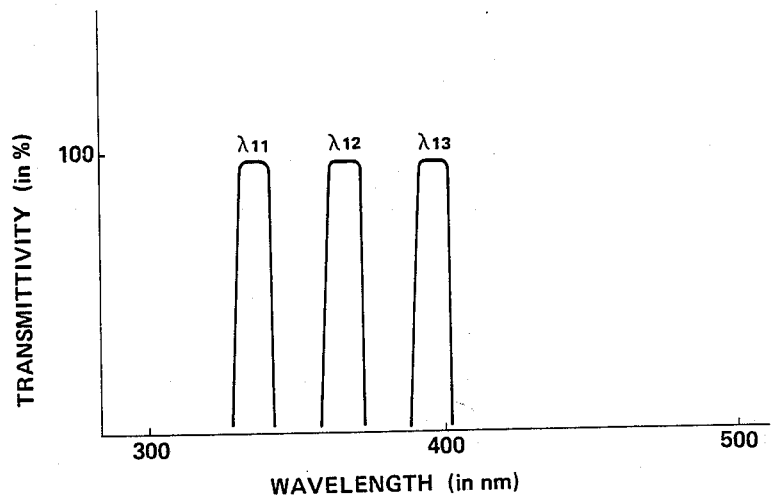

On the other hand, in the special light rotary color filter 131 for the special picture images, filters 134a, 134b and 134c transmitting the lights in the narrrow bands with such wavelengths $\lambda_{11}$, $\lambda_{12}$ and $\lambda_{13}$ as are shown in FIG. 29 as centers are arranged in the peripheral direction as shown in FIG. 27.

Not only the body outside light observing switch 47 but also the special light observing switch 136 is connected to the fiter moving motor 31. When the on-signal is input from this special light observing switch 136, the filter moving motor 31 will retreat the rotary color filter 24 for the visible light observation from the illuminating light path and will insert the special light rotary color filter 131 into the illuminating light path and the light from the light source lamp 22 will be separated into the lights of the wavelength bands shown in FIG. 29.

The separated illuminating lights of the wavelength bands $\lambda_{11}$, $\lambda_{12}$ and $\lambda_{13}$ are radiated onto the inner wall 20 of the body cavity through the light guide 29. The returning lights from the inner wall 20 of the body cavity have such data of the object as can not be obtained with the visible lights R, G and B and form an image on the solid state imaging device 34 through the objective lens system 33 the same as the visible lights. Thereafter, the same signal processing as with the visible lights is made. For example, the picture image data based on the wavelength $\lambda_{11}$ are written into the frame memory 43R, the picture image data based on the wavelength $\lambda_{12}$ are written into the frame memory 43G and the picture image data based on the wavelength $\lambda_{13}$ are written into the frame memory 43B, respectively.

Then, the picture image data are simultaneously read out of the respective frame memories and are displayed in the monitor 6. In the picture image data output from the respective frame memories 43, red (R) corresponds to the wavelength $\lambda_{11}$, green (G) corresponds to the wavelength $\lambda_{12}$ and blue (B) corresponds to the wavelength $\lambda_{13}$, respectively. The display in the monitor 6 becomes a quasi-color moving picture as a normal observing picture image.

On the other hand, when the body outside light observing switch 47 is switched on, the filter moving motor 31 will retreat the special light rotary filter 131 or the rotary color filter 24 for visible lights out of the illuminating light path and will increase the light amount fed to the endoscope 2. By the increase of the light amount, a part of the light radiated onto the inner wall 20 of the body cavity will be transmitted out of the body so that the position of the tip part 11 may be confirmed.

In this case, the same as in the first embodiment, by the on-signal from the body outside light observing switch 47 the control circuit 46 will switch the switches 48 and 49 to display in the monitor 6 a moving picture of a black and white picture image by a G monochrome which is a picture image different from the normal observing picture image.

In this embodiment, the normal observation is an observation with a visible light and another special light than the visible light and the ordinary observing picture image is a color moving picture obtained with a visible light and a quasi-color moving picture obtained with another special light than the visible light.

The other formations and operations are the same as of the first embodiment.

FIGS. 30 and 31 show the tenth embodiment of the present invention.

In this embodiment, the same as in the ninth embodiment, the present invention is applied to an endoscope apparatus making a special light observation.

The solid state imaging device 34 provided in the tip part 11 of the insertable part 7 of the endoscope 2 of this embodiment has a sensitivity in a wide wavelength range from the ultraviolet region to the infrared region including the visible region. Signal lines 141 and 142 are connected to the above mentioned solid state imaging device 34 and to the signal processing circuit.

On the other hand, a lamp 143 emitting lights in a wide band from ultraviolet rays to infrared rays is provided within the control apparatus 4 and may be a general xenon lamp or strobe lamp which emits a large amount of not only a visible light but also ultraviolet rays and infrared rays. This lamp 143 is fed by a power source part 144 with an electric power. A rotary filter 147 rotated and driven by a motor 146 is arranged in front of the above mentioned lamp 143 and has two concentrically sectioned parts as shown in FIG. 31. On the outer peripheral part side of the rotary filter 147, visible light observing filters 133a, 133b and 133c transmitting the lights of the wavelength regions of red (R), green (G) and blue (B) are arranged in the peripheral direction and, on the inner peripheral part side, special light observing filters 134a, 134b and 134c transmitting the lights of the narrow bands with the wavelengths $\lambda_{11}$, $\lambda_{12}$ and $\lambda_{13}$ as centers are arranged in the peripheral direction. A fan-shaped light intercepting part 148 having a black and white filter 149 is provided in the outer peripheral edge part of the rotary filter 147.

By the way, the transmitting characteristics of the above mentioned filters 134a, 134b and 134c are shown in FIG. 28. The wavelengths $\lambda_{11}$, $\lambda_{12}$ and $\lambda_{13}$ are set as shown in FIG. 29. That is to say, a set of such wavelength groups for special picture images as of $\lambda_{11}$, $\lambda_{12}$ and $\lambda_{13}$ is a combination of such wavelength at which the light absorbing degree of the blood varies with the variation of the oxygen saturation degree (mentiond also as $SO_2$) of hemoglobin as, for example, $\lambda_{12}$, and such wavelengths which are near that wavelength and at which the light absorbing degree of the blood varies little with the variation of the $SO_2$ as, for example, $\lambda_{11}$ and $\lambda_{13}$ as shown in FIG. 32.

Figure 32:
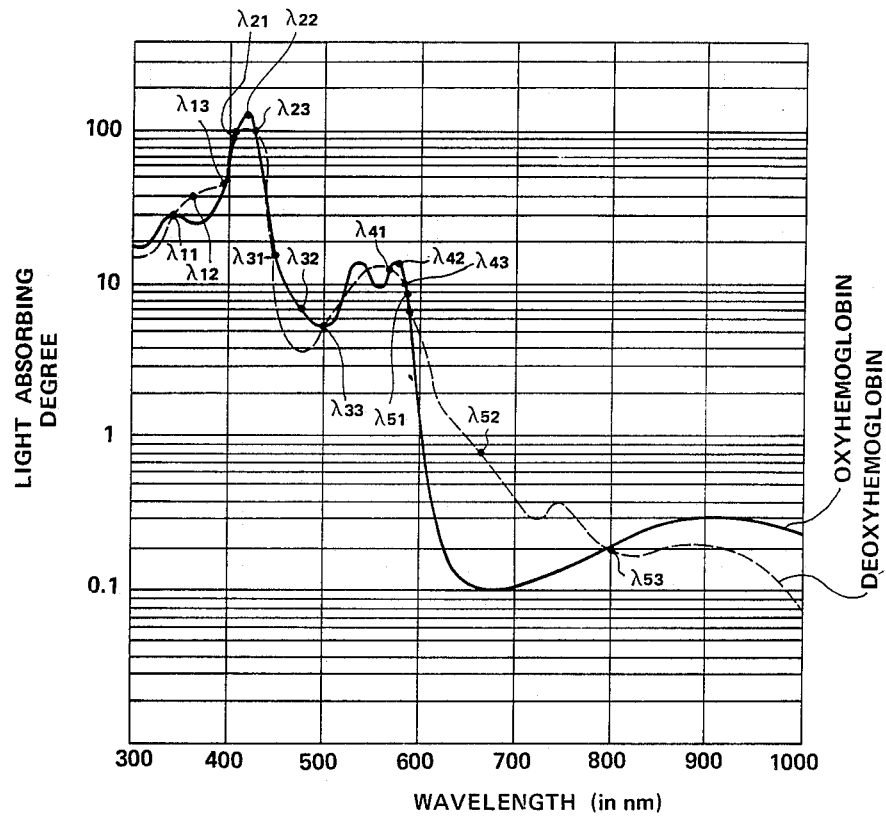

By the way, in FIG. 32, in order to show the variation of the light absorbing degree of the blood with the variation of the $SO_2$, the spectral light absorption characteristics of oxyhemoglobin and deoxyhemoglobin are shown.

As shown in FIG. 32, in 300 to 1000 nm., as wavelength groups for special picture images, there can be set not only the above mentioned $\lambda_{11}$, $\lambda_{12}$ and $\lambda_{13}$ in 300 to 400 nm. but also $\lambda_{21}$, $\lambda_{22}$ and $\lambda_{23}$ near 400 nm., $\lambda_{31}$, $\lambda_{32}$ and $\lambda_{33}$ in 400 to 500 nm., $\lambda_{41}$, $\lambda_{42}$ and $\lambda_{43}$ in 500 to 600 and $\lambda_{51}$, $\lambda_{52}$ and $\lambda_{53}$ in 450 to 850. The transmitted wavelengths of the filters 134a, 134b and 134c of the above mentioned rotary filter 147 are not limited to the above mentioned $\lambda_{11}$, $\lambda_{12}$ and $\lambda_{13}$ but any wavelength group can be selected from among the above described five wavelength groups.

The above mentioned motor 146 is controlled in the rotation and is driven by a motor driver 151.

In this embodiment, a filter switching apparatus 153 controlled by a control signal from a switching circuit 152 is provided and selectively interposes any part of the outer peripheral part, inner peripheral part and light intercepting part 148 of the above mentioned rotary filter 147 by varying the positions of the above mentioned rotary filter 147 and motor 14 with respect to the optical axis of the illuminating light path between the lamp 143 and the entrance end of the light guide 29.

The light transmitted through the above mentioned rotary filter 147 and separated in time series into lights of the respective wavelength regions within the selected wavelength group enters the above mentioned light guide 29 at the entrance end, is led to the tip part 11 through this light guide 29 and is emitted from this tip part 11 to illuminate the observed part.

The returning light from the observed part by this illuminating light is made to form an image on the solid state imaging device 34 by the objective lens system 33 and is photoelectrically converted. Driving pulses from the driver circuit 36 within the above mentioned control apparatus 4 are applied to this solid state imaging device 34 through the above mentioned signal line 141 and the reading-out and transfer are made by these driving pulses. The video signal read out of this solid state imaging device 34 is input into a preamplifier 37 provided within the above mentioned control apparatus 4 or the endoscope 2 through the above mentioned signal line 142. The video signal amplified by this preamplifier 37 is input into a processing circuit 154, is subjected to such signal processing as $\gamma$ correction and white balancing and is converted to a digital signal. This digital video signal is selectively memorized by the multiplexer 42 into three memories 43a, 43b and 43c corresponding to the respective colors, for example, of red (R), green (G) and blue (B). The signals are simultaneously read out of the above mentioned memories 43a, 43b and 43c, are converted to analogue signals by the D/A converter 44, are output as R, G and B color signals and are input into a matrix circuit 156 from which a luminance signal Y and color difference signals R-Y and B-Y are produced. The luminance signal Y is input into the mixer 91 and the color difference signals R-Y and B-Y are input into the encoder 103. The color difference signals R-Y and B-Y are made a chroma signal in the encoder 103 and the chroma signal is input into the input terminal 104a of the output switch 104 of two inputs and one output. In case no control signal from the switching circuit 152 is input into the switch 104 of two inputs and one output, the input terminal 104a and output terminal 104c will be connected with each other and the input chroma signal will be input into the mixer 91. In the mixer 91, a composite signal is produced of the luminance signal Y and chroma signal and is input into the color monitor 6.

A timing generator 157 for timing of the entire system is provided within the above mentioned control apparatus 4 and such respective circuits as of the motor driver 151, driver circuit 36 and multiplexer 42 are synchronized by this timing generator 157.

By the way, a part of the video signal output from the processing circuit 154 is transmitted to an exposure controlling circuit 158 in which a throttle 159 provided between the lamp 143 and rotary filter 147 is controlled from this video signal so that the light emitted from the lamp 143 may be of a proper light amount.

In this embodiment, when a visible light observing signal is input from the switching circuit 152, the filter controlling apparatus 153 will interpose in the illuminating light path the visible light observing filters 133a, 133b and 133c transmitting R, G and B of the rotary filter 147. Then, the light emitted from the above mentioned lamp 143 will sequentially pass through the filters 133a, 133b and 133c and will be divided in time series into lights of the respective wavelength regions of R, G and B. These lights of R, G and B are transmitted to the tip part 11 through the light guide 29 and are radiated onto the object. The returning lights from the object by the frame sequential illuminating lights of R, G and B in this visible band are made to form an image on the solid state imaging device 34 by the objective lens system 33 and the object image is imaged by this solid state imaging device 34. Therefore, a color moving picture based on the visible light which is a normal observing picture image is displayed in the monitor 6.

On the other hand, when a signal for observing another special light other than the visible light is input from the above mentioned switching circuit 152, the filter switching apparatus 153 will interpose the special light observing filters 134a, 134b and 134c in the illuminating light path. Then, the light emitted from the above mentioned lamp 13 will be divided in time series into the lights of the wavelength groups ($\lambda_{11}$, $\lambda_{12}$ and $\lambda_{13}$) of the above mentioned rotary filter 147. These lights are transmitted to the tip part 11 through the light guide 29 and are radiated onto the object. The returning lights from the object by these illuminating lights are made to form an image on the solid state imaging device 34 by the objective lens system 33 and the object image is imaged by this solid state imaging device 34. Thereafter, the same as in the visible light, the lights are processed to be signals and a quasi-color picture image by the wavelength groups ($\lambda_{11}$, $\lambda_{12}$ and $\lambda_{13}$) is displayed in the monitor 6. With this picture image, the variation of the $SO_2$ and hemoglobin amounts can be observed.

By the way, when one or two of the memories 43a, 43b and 43c are selectively read out, a picture image by one or two wavelength regions of the above mentioned wavelength groups will be able to be obtained.

When a special light picture image is selected, the R, G and B signals from the above mentioned video processor 6 will be processed and a picture image showing the $SO_2$ and hemoglobin amounts will be able to be obtained.

Further, when a body outside light observing signal is input into the filter switching apparatus 153 from the switching circuit 152, the filter switching apparatus 153 will switch the switch 104, the input terminal 104a and the output terminal 104b open or connected to the GND will be connected with each other and the light intercepting part 148 of the rotary filter 147 will be inserted into the illuminating light path. As the rotary filter 147 is rotated and driven by the motor 146, the case that the illuminating light emitted from the lamp 143 directly enters the light guide 29, the case that the light is intercepted by the light intercepting part 148 and the case that the light passes through the black and white filter 149 provided in the light intercepting part 148 and enters the light guide 29 occur periodically. In the case that the light directly enters the light guide 29, the light will not pass through the filter and therefore the light amount will be larger than in the case of the visible light observation or special light observation. When the illuminating light increases, the illuminating light radiated onto the object from the light guide 29 will go out of the body through the inner wall of the body cavity and the position of the tip part 11 of the endoscope 2 will be able to be confirmed from outside the body. The returning light from the inner wall 20 of the body cavity forms an image on the solid state imaging device 34 through the objective lens 33 and is processed as an electric signal in the processing circuit 154.

Here, as the output terminal 104b side is selected in the switch 104, the chroma signal will not be output to the mixer 91 but only the luminance signal Y will be output to the monitor 6 in which a black and white moving picture image which is a picture image different from the normal observing picture image will be displayed on the basis of this luminance signal.

Then, in case the illuminating light passes through the black and white filter 149, an illuminating light amount adapted to display a black and white moving picture in the monitor 6 will be fed to the light guide 29. Therefore, a clear black and white moving picture will be displaYed in the monitor 6. By the way, in this case, too, as a control signal is output to the switch 104 from the switching circuit 152, the output terminal 104b side will be selected.

In this embodiment, as a visible light observation, special light observation and body outside light observation can be made with one rotary filter 147, the control apparatus described in the ninth embodiment can be made small. The other effects are the same as of the first embodiment.

By the way, the black and white filter 149 may be a filter conforming to the spectral sensitivity characteristics of the solid state imaging device 34 and light source and the visibility characteristics of the standard observer or may be a filter which will remove the light on the short wavelength side not passing substantially through the living body in case the body outside light observation is made in the other outer peripheral edge part than is provided with the light intercepting part 148 of the rotary filter 147.

Further, in case the illuminating light is fed directly to the light guide 29 from the lamp 143 by the exposure controlling circuit 158 and throttle 159, the light amounnt may be increased and, in case the illuminating light passes through the black and white filter 149, a proper exposure may be obtained.

Figure 33:
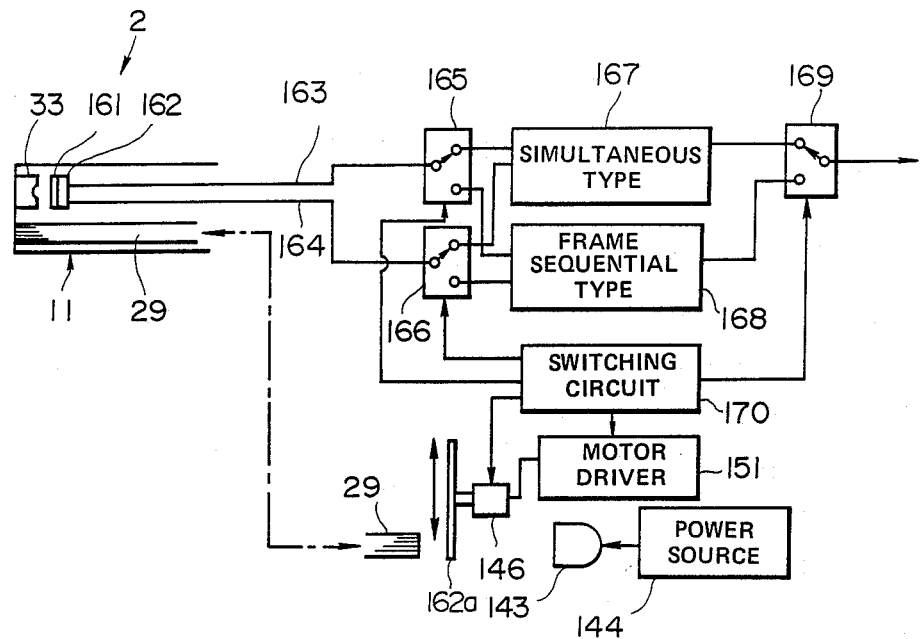
FIGS. 33 and 34 relate to the 11th embodiment of the present invention.
Figure 34:
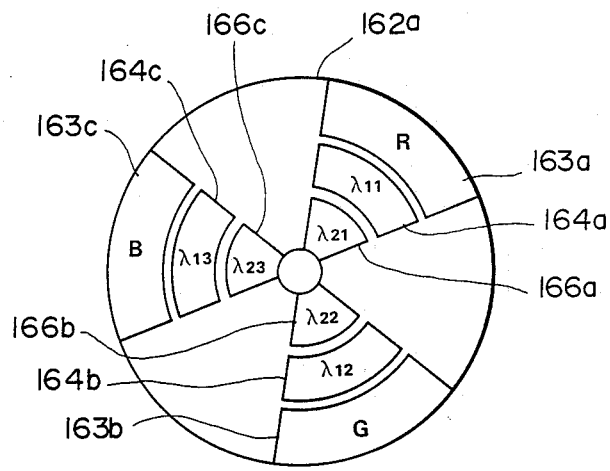
Figure 35:
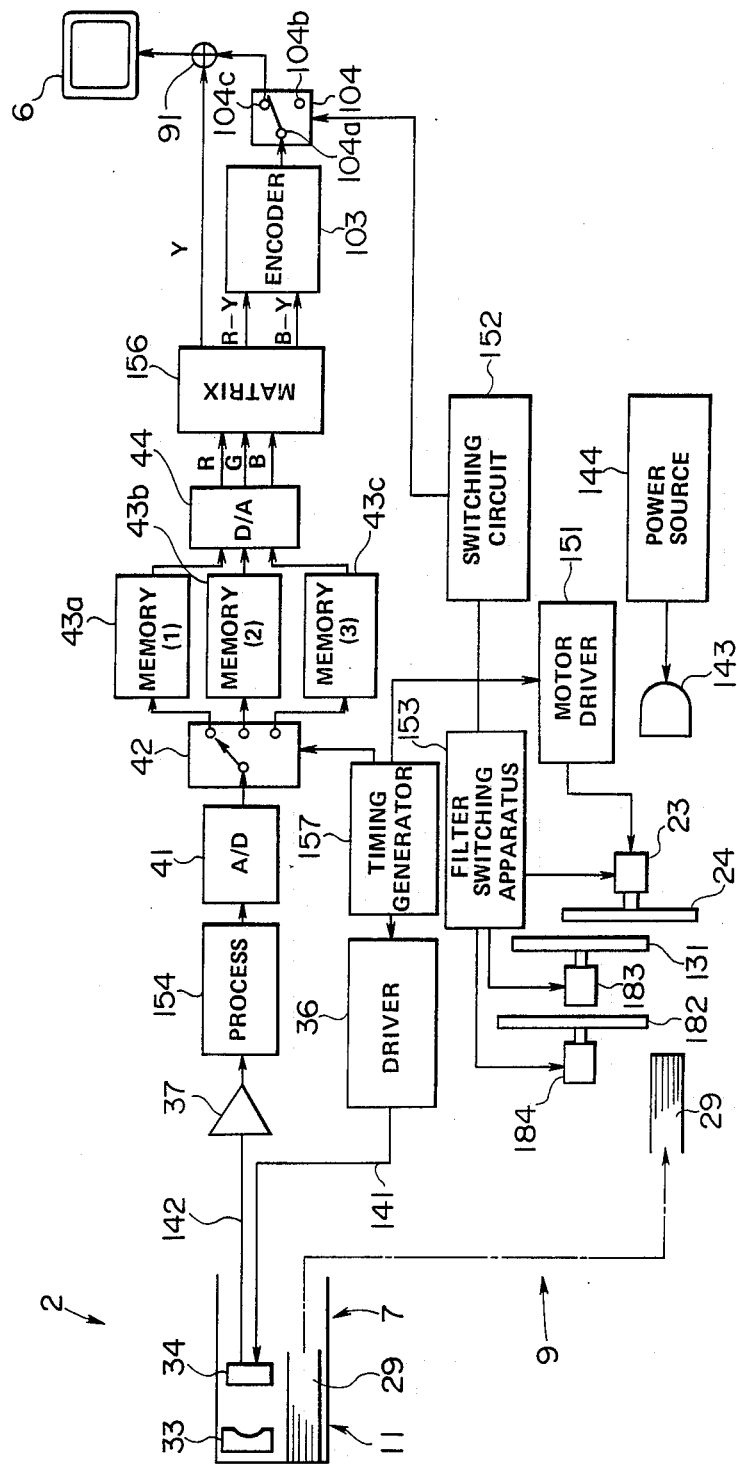
FIGS. 35 and 38 relate to the 12th embodiment of the present invention.
Figure 36:
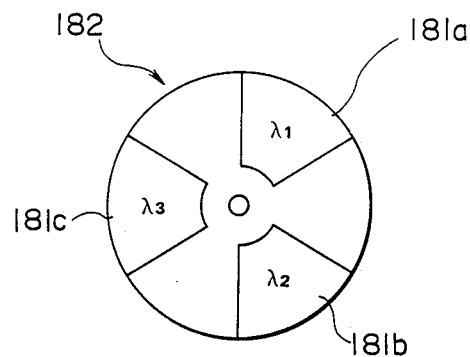
FIG. 36 is a contour view of a rotary filter for special observation.

FIGS. 33 and 34 show the 11th embodiment of the present invention.

In this embodiment, a simultaneous type signal processing circuit and a frame sequential type signal processing circuit are provided, the frame sequential type signal processing circuit is operated in the visible light observation and special light obsevation and the simultaneous type signal processing circuit is operated in the body outside light observation.

In this embodiment, a solid state imaging device 162 provided on the front surface with a body outside light observing color filter array 161 of a complementary color system is arranged in the image forming position of the objective lens system 33 in the tip part 11 of the insertable part of the endoscope 2. A driving pulse transmitting signal line 163 and output signal transmitting signal line 164 are connected to this solid state imaging device 162 and are connected respectively to the simultaneous type signal processing circuit 167 and frame sequential type signal processing circuit 168 respectively through selectors 165 and 166. Either of the output signal of the above mentioned simultaneous type signal processing circuit 167 and the output signal of the frame sequential type signal processing circuit 168 is selected by a selector 169 and is output to the signal processing circuit in the later step. By the way, the above mentioned selectors 165, 166 and 169 are all switched to the simultaneous type side or frame sequential type side by a switching circuit 170.

On the other hand, in the light source part, a rotary filter 162a has three concentrically sectioned parts as shown in FIG. 34. In the outermost peripheral part, visible light observing filters 163a, 163b and 163c transmitting respectively the lights of the wavelength regions of red (R), green (G) and blue (B) are arranged in the peripheral direction, in the central part, special light observing filters 164a, 164b and 164c transmitting respectively the lights of the narrow bands with the wavelengths $\lambda_{11}$, $\lambda_{12}$ and $\lambda_{13}$ as centers are arranged in the peripheral direction and, in the innermost peripheral part, special light observing filters 166a, 166b and 166c transmitting respectively the lights of the narrow bands with the wavelengths $\lambda_{21}$, $\lambda_{22}$ and $\lambda_{23}$ as centers are arranged in the peripheral direction.

By the way, the wavelengths $\lambda_{11}$, $\lambda_{12}$, $\lambda_{13}$, $\lambda_{21}$, $\lambda_{22}$ and $\lambda_{23}$ transmitted respectively by the above mentioned filters 164a, 164b, 164c, 166a, 166b and 166c are the same as the wavelengths described in the tenth embodiment.

The above mentioned rotary filter 162a and motor 146 are changed in position with respect to the optical axis of the illuminating light path by the above mentioned switching circuit 170. By the way, in this embodiment, the above mentioned rotary filter 162a can be perfectly retreated from the illuminating light path.

In this embodiment, in the case of the visible light observation or in the case of the special light observation observing the variations of the oxygen saturation degree and amount of hemoglobin in the blood and the blood flow volume, the above mentioned rotary filter 162a is interposed in the illuminating light path, the illuminating light is color-separated in time series, the frame sequential type signal processing circuit 168 side is selected and the frame sequential type signal processing is made to obtain moving pictures of a quasi-color picture image which is a normal observing picture image and a color picture image.

Further, in the case of the body outside light observation, the rotary filter 162a is pulled out of the illuminating light path and the light amount of the illuminating light fed to the light guide 29 is increased. In this case, the switching circuit 170 switches the selectors 165 and 166 to the simultaneous type side and the signal is processed by the simultaneous type signal processing circuit 167. The displayed picture image in the monitor 6 in this case is a color moving picture which is obtained from the simultaneous type signal processing circuit 167 and is a picture image different from the normal observing picture image.

In this embodiment, when the rotary filter 162a is pulled out of the illuminating light path, the light amount of the illuminating light which is a white light radiated onto the inner wall of the body cavity will increase, a part of the light will pass out of the body and the position of the tip part 11 can be known. As the solid state imaging device 162 is provided with the color filter array 161 and further the simultaneous type signal processing circuit 167 operates, even if the illuminating light is a white light, the picture image in the monitor 6 will display a color moving picture.

The other formations, operations and effects are the same as of the first embodiment.

FIGS. 35 to 38 show the 12th embodiment of the present invention.

In this embodiment, infrared rays having passed through the inner wall of the body cavity are photographed with an infrared ray camera directed to the body outside to confirm the position of the tip part of the endoscope.

By the way, the formation of the electronic endoscope apparatus 1 is the same as of the tenth embodiment except that three rotary filters are provided.

This embodiment comprises not only the electronic endoscope apparatus 1 but also an infrared ray camera 176, a camera control unit 177 for controlling this infrared ray camera 176, a monitor 178 for displaying a picture image obtained by the infrared ray camera 176 and a timing generator 179 for adjusting the timing on the electronic endoscope apparatus 1 side and infrared ray camera 176.

The same as in the tenth embodiment, the electronic endoscope apparatus 1 is provided with a filter switching apparatus 153 by which three rotary filters 24, 131 and 182 are selected and are inserted in the illuminating light path.

The above mentioned rotary filter 24 for a visible light is formed as in FIG. 26 of the ninth embodiment and the rotary filter 131 is formed as in FIG. 27.

The above mentioned filters 24, 131 and 182 are rotated and driven respectively by motors 23, 183 and 184.

By the way, though not illustrated, the motors 183 and 184 are respectively driven by a motor driver 151 controlled by the timing generator 157 the same as in the motor 23.

Figure 37:
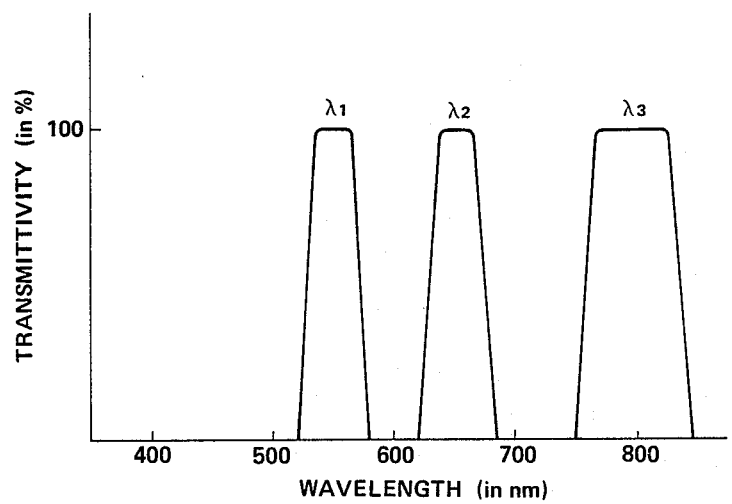
FIG. 37 is an explanatory view showing a spectral transmitting characteristic in FIG. 36.
Figure 38:
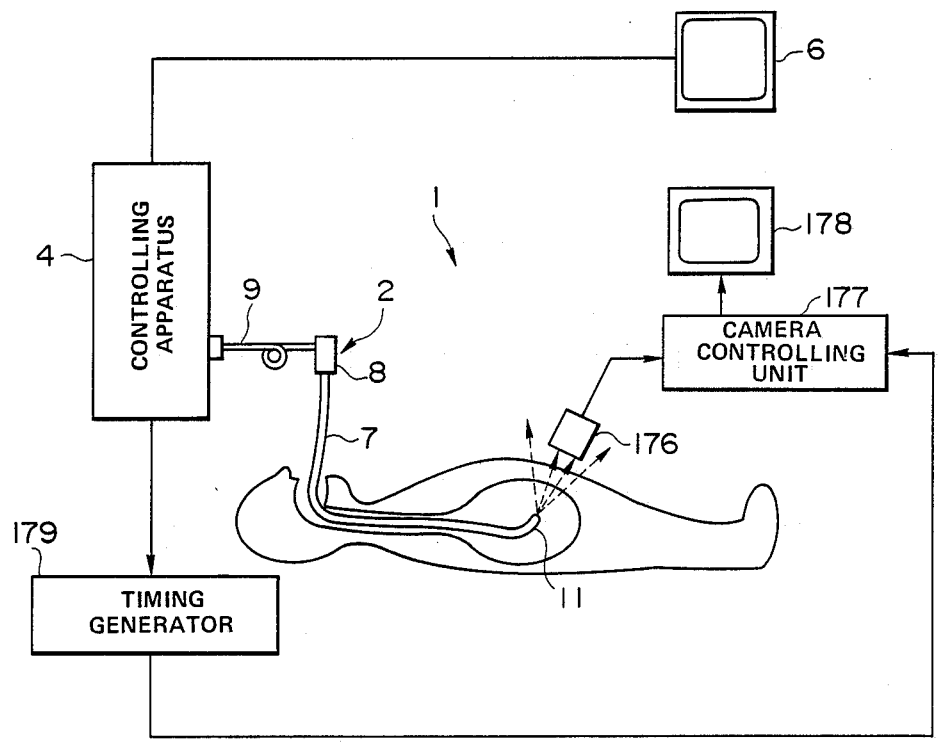

In the above mentioned special light observing rotary filter 182, filters 182a, 182b and 182c transmitting the lights of the narrow bands having wavelengths $\lambda_1$, $\lambda_2$ and $\lambda_3$ as centers as shown in FIG. 37 are arranged in the peripheral direction.

By the way, the combination of the above mentioned wavelengths $\lambda_1$, $\lambda_2$ and $\lambda_3$ may be any of five wavelength groups of such $\lambda_{11}$, $\lambda_{12}$ and $\lambda_{13}$ as in FIG. 32. However, the combination of the transmitted wavelength ranges of the respective filters is different between the rotary filter 131 and rotary filter 182.

In this embodiment, when any one of the visible light observing rotary filter 24 and two special light observing rotary filters 131 and 182 is selectively inserted into the illuminating light path by the filter switching apparatus 153, the picture image based on the visible light and the picture image showing the variations of the oxygen saturation degree and amount of hemoglobin and the blood flow volume in the blood in different wavelength regions will be able to be switched and observed.

On the other hand, the position of the tip part 11 of the endoscope 2 is confirmed in the case that the rotary filter 182 is in the illuminating light path. That is to say, the light of the wavelength $\lambda_3$ obtained by the filter 182a comes out of the body through the inner wall of the body cavity. Outside the body, the infrared ray camera 176 is in the position of obtaining the light transmitted from within the body and photographs this image. The photographed image is transmitted to the camera control unit 177 and the position of the tip part 11 is displayed in the monitor 178. The picture image displayed in the monitor 178 is a black and white moving picture based on the light of the wavelength $\lambda_3$ and different from the normal observing picture image.

By the way the control apparatus 4 applies a clock to the timing generator 179 which outputs by this clock to the camera control unit 177 a timing signal synchronized with the rotary filter 182. The camera control unit 177 controls the shutter not illustrated of the infrared ray camera 176 to receive the light with the filter 182a only in case the light of the wavelength $\lambda_3$ is radiated so that the transmitted light from within the body may be received at a favorable S/N ratio.

By the way, in this embodiment, the monitor 6 for the normal light observation and the monitor 178 for the body outside light observation are separate from each other but an infrared ray image may be superimposed on the monitor 6 for the normal light observation.

By the way, the number of the rotary filters selectively inserted in the illumination light path is not limited to be three but may be a plurality.

The other formations, operations and effects are the same as of the first embodiment.

Figure 39:
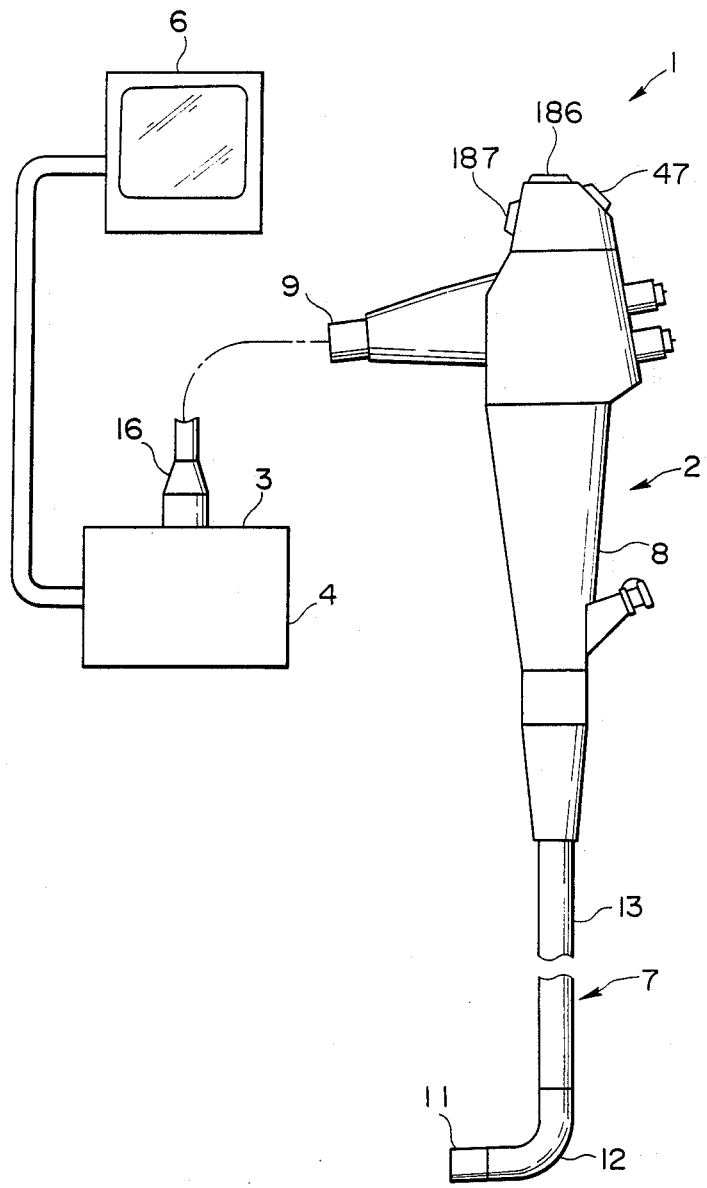
FIG. 39 relates to the 13th embodiment of the present invention and is an explanatory view of an electronic endoscope provided with a body outside light observing apparatus.

FIG. 39 shows the 13th embodiment of the present invention.

In this embodiment, the body outside light observing switch 47 is provided in the operating part 8 of the endoscope 2.

The operating part 8 of the endoscope 2 of this embodiment is provided at the rear end with a freezing switch 186 for making the picture image in the monitor 6 a still picture image, a releasing switch 187 for recording the frozen picture image and the body outside light observing switch 47 described in the first embodiment.

By thus providing the body outside light observing switch 47 in the operating part 8, its operability can be made better than in the case of providing it in the control apparatus 4.

Figure 40:
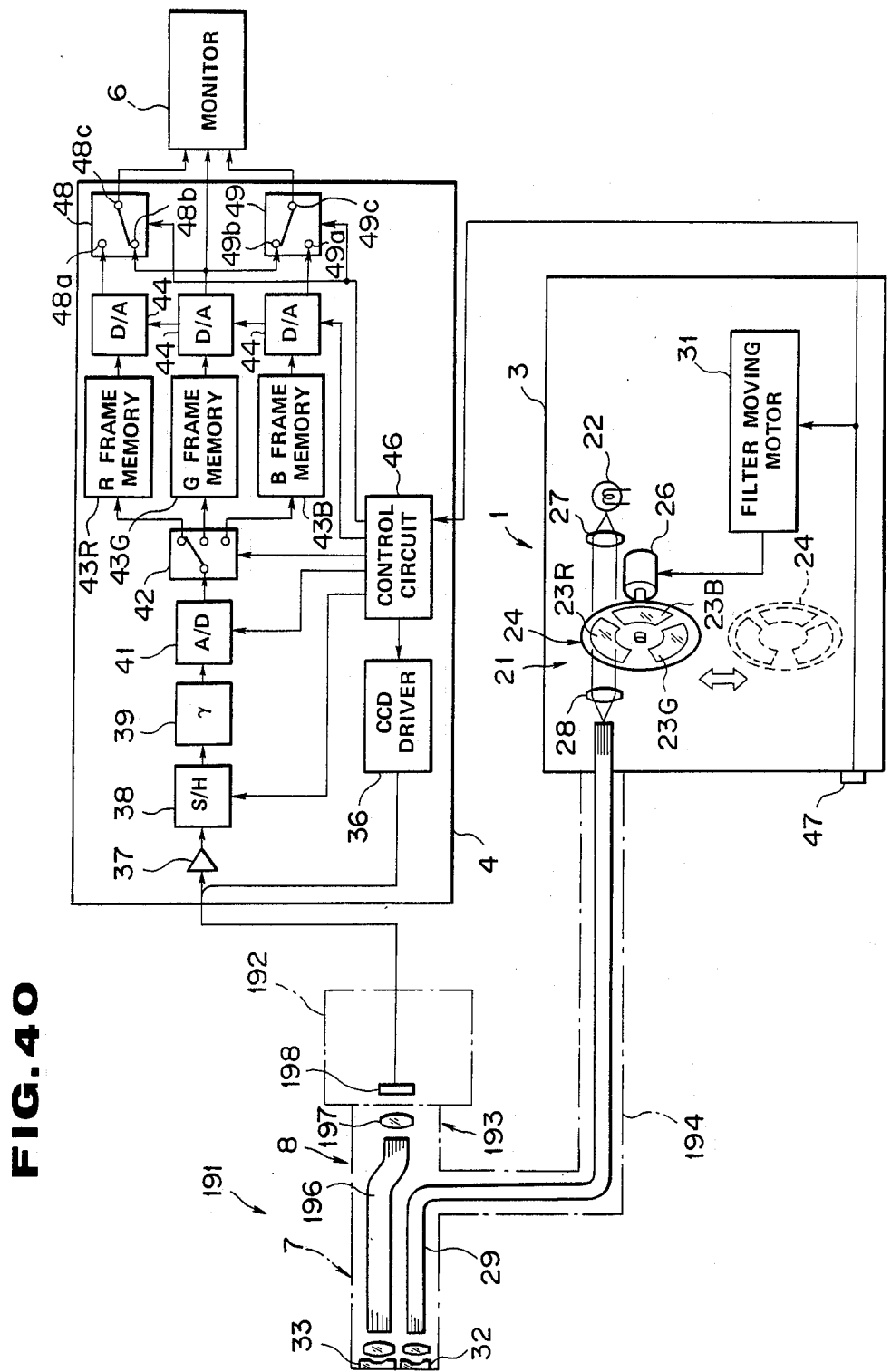
FIG. 40 relates to the 14th embodiment of the present invention and is an explanatory view showing the formation of an electronic endoscope apparatus.

FIG. 40 shows the 14th embodiment of the present invention.

In this embodiment, an optical endoscope 191 is fitted with a frame sequential type externally fitted TV camera 192.

By the way, the formations of the control apparatus 4 and light source apparatus 3 are the same as in the first embodiment.

The optical endoscope 191 comprises an insertable part 7, an operating part 8 connected to the rear of this insertable part 7 and an eyepiece part 193 provided at the rear end of this operating part 8. A universal cord 194 is extended from the side of the operating part 8. An objective lens system 33 and light distributing lens system 32 are provided in the tip part 11 of the insertable part. The entrance end surface of an image guide 196 is provided in the image forming position of the objective lens system 33. This image guide 196 is inserted through the insertable part 7 and operating part 8 and its exit end surface comes to the eyepiece part 193. The externally fitted TV camera 192 is removably fitted to the eyepiece part 193 and is provided with a solid state imaging device 198 which can image an optical image transmitted through an eyepiece lens 197 provided in the eyepiece part 193. This solid state imaging device 198 outputs to the preamplifier 37 an electric signal obtained by converting an optical image by the CCD driver 36 of the control apparatus 4.

In this embodiment, the normal observing picture image is a color moving picture and, in case the rotary filter 24 is retreated out of the illuminating light path to make a body outside light observation, the displayed picture image in the monitor 6 will become a black and white moving picture which is a picture image different from the ordinary observing picture image.

The other formations, operations and effects are the same as of the first embodiment.

Figure 41:
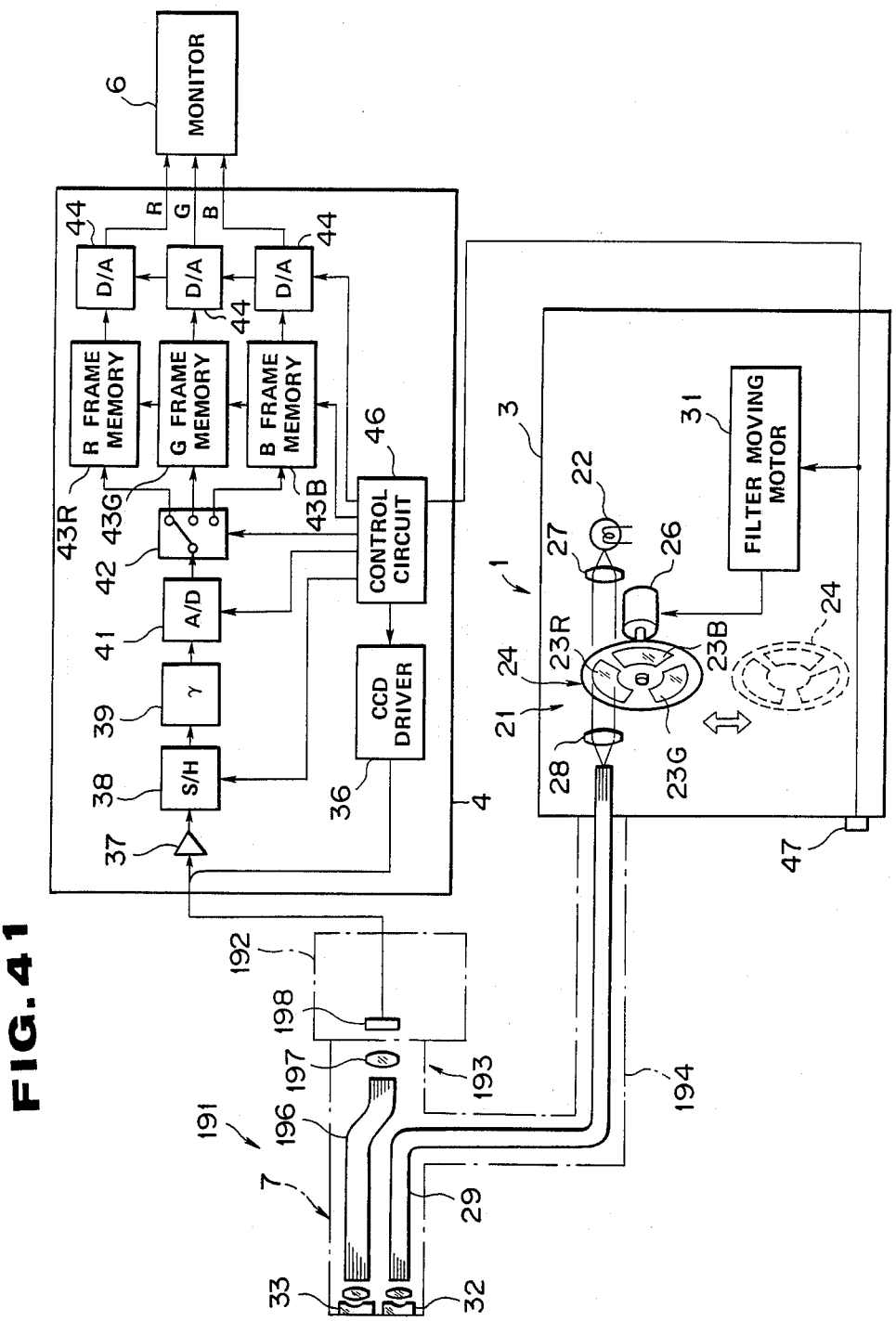
FIG. 41 relates to a modification of the 14th embodiment and is an explanatory view showing the formation of an electronic endoscope apparatus.

FIG. 41 is of a modification of the 14th embodiment.

In this modification, the control apparatus 4 and light source apparatus 3 described in the fifth embodiment are connected to the optical endoscope 191 and frame sequential type externally fitted TV camera 192 described in the 14th embodiment.

In this embodiment, the normal observing picture image is a color moving picture and, in case the rotary filter is retreated out of the illuminating light path to make a body outside light observation, the display in the monitor 6 will be a color still picture which is a picture image different from the normal observing picture image.

The other formations, operations and effects are the same as of the first embodiment.

Figure 42:
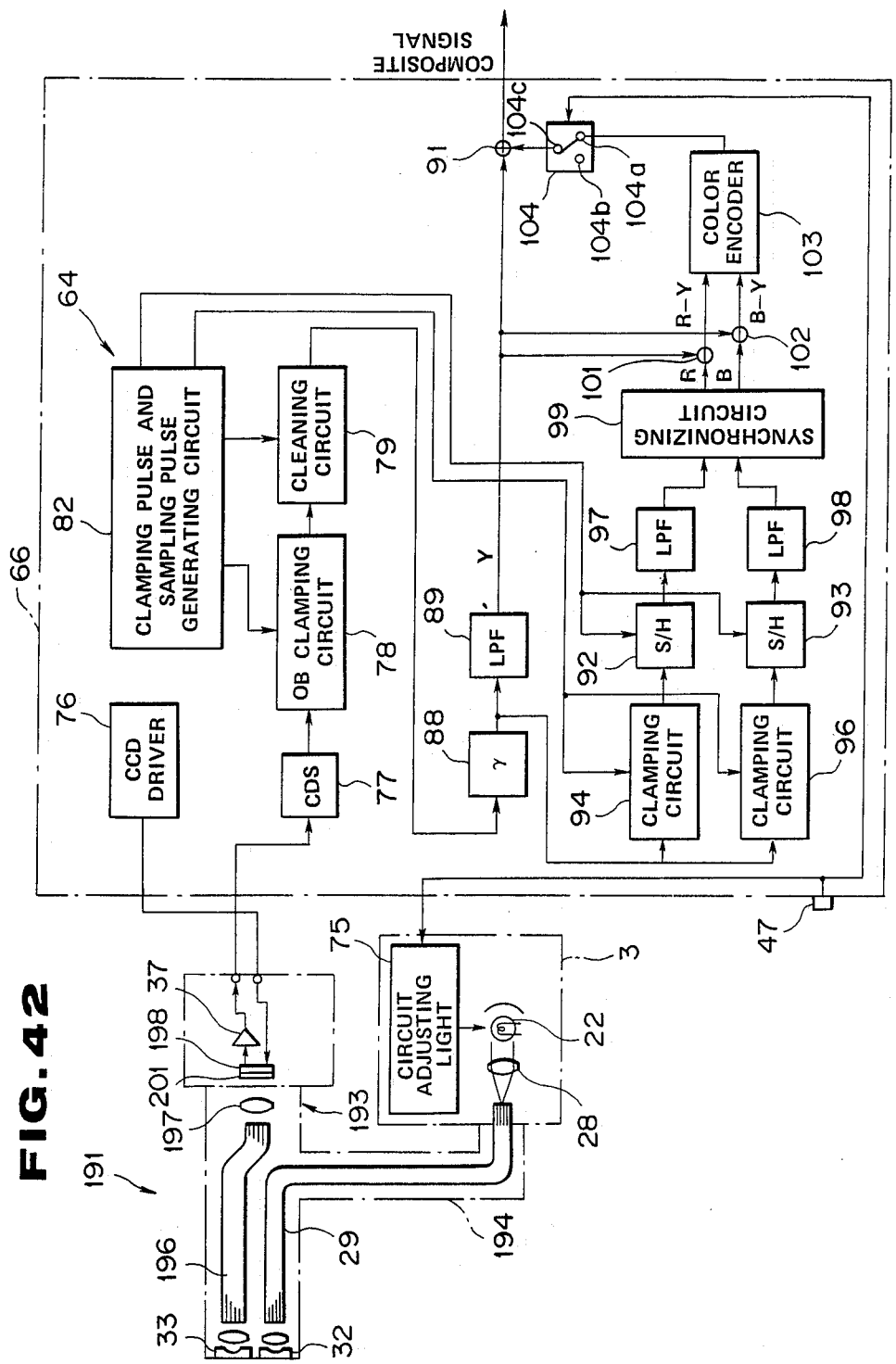
FIG. 42 relates to the 15th embodiment of the present invention and is an explanatory view showing the formation of an electronic endoscope apparatus.

FIG. 42 shows the 15th embodiment of the present invention.

In this embodiment, a simultaneous type externally fitted TV camera 199 is removablly fitted to the optical endoscope 191 described in the 14th embodiment.

By the way, the formation of the control apparatus 66 is the same as of the second embodiment.

A color separating filter 201 provided in the form of a mosaic with filters separating the incident light into the colors for example, of red (R), green (G) and blue (B) is fixed on the imaging surface of the solid state imaging device 198 contained in the simultaneous type externally fitted TV camera 199.

The light source apparatus 3 feeding an illuminating light to the optical endoscope 191 comprises a light source lamp 22 for outputting a light, a condenser lens 28 for condensing the light emitted from this light source lamp 22 and radiating it onto the entrance end surface of the light guide 29 and a light adjusting circuit 75 for increasing the light amount output by the light source lamp 22 in the case of making a body outside light observation.

In this embodiment, the normal observing picture image is a color moving picture and, in the case of making a body outside light observatiion, the display in the monitor 6 will be a black and white moving picture different from the normal observing picture image.

Figure 43:
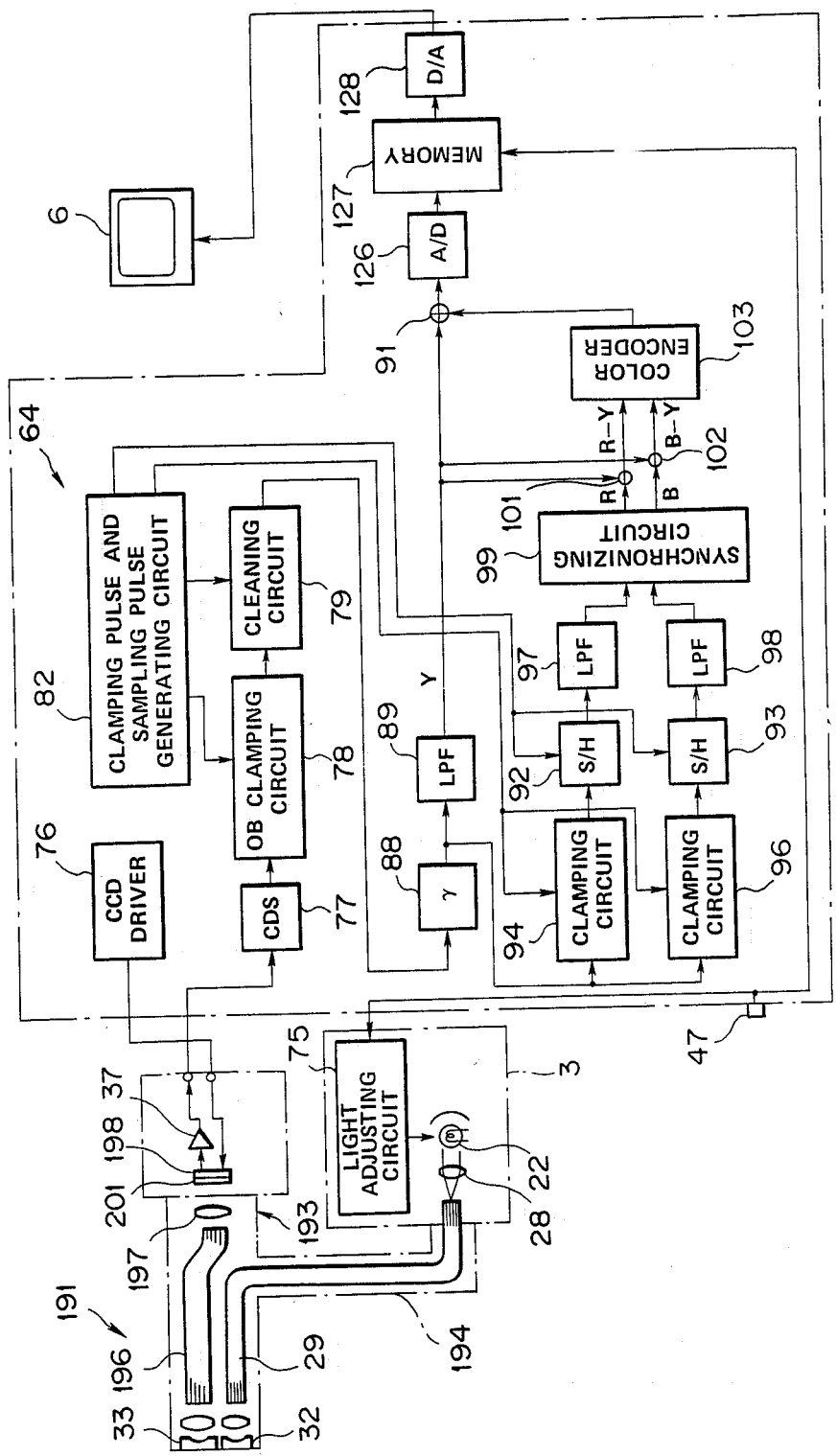
FIG. 43 relates to a modification of the 15th embodiment and is an explanatory view showing the formation of an electronic endoscope apparatus.

FIG. 43 is of a modification of the 15th embodiment.

This modification is formed of the optical enddoscope 191 and simultaneous type externally fitted TV camera 199 described in the 15th embodiment and the control apparatus 66 described in the third embodiment.

In this modification, the ordinary observing picture image is a color moving picture and, in case a body outside light observation is made, the display in the monitor 6 will be a color still picture different from the normal observing picture image.

What is claimed is:

1. An electronic endoscope apparatus whereby, when a light emitted from an illuminating window provided in a tip part of an insertable part inserted into a body cavity is transmitted out of the body from within the body cavity, the position of said tip part will be confirmed from outside the body, comprising:

an imaging means for producing an image of an inspected part obtained from an observing window provided in the tip part of said insertable part, and for converting this image to an electric signal and outputting it;

an illuminating means for feeding an illuminating light to said imaging means and for adjusting the brightness of the illuminating light when a confirming signal directing the confirmation of the position of the tip part of said insertable part is input;

a signal processing means for processing the electric signal obtained from said imaging means, outputting a video signal which is an ordinary observing picture image signal of a moving picture in case said confirming signal is not input and outputting a video signal which is a picture image signal different from said ordinary observing picture image signal in case said confirming signal is input; and a displaying means for receiving said video signal output by said signal processing means and displaying the picture image of the inspected part.

2. An electronic endoscope apparatus according to claim 1 wherein said ordinary observing picture image is a picture image which is a color moving picture.

3. An electronic endoscope apparatus according to claim 1 wherein said ordinary observing picture image is a picture image which is a color moving picture and a moving picture imaged with an illuminating light other than a visible light.

4. An electronic endoscope apparatus according to claim 1 wherein said ordinary observing picture image is a picture image based on the video signal processed by a frame sequential type signal processing circuit.

5. An electronic endoscope apparatus according to claim 1 wherein said imaging means comprises an optical endoscope having an image guide means transmitting to an eyepiece part the optical image obtained through said observing window and an externally fitted television camera having a solid state imaging device fitted to said eyepiece part and imaging the optical image transmitted by said image guide means.

6. An electronic endoscope apparatus according to claim 1 wherein said imaging means is an electronic endoscope having a solid state imaging means forming the optical image obtained through said observing window and converting it to an electric signal.

7. An electronic endoscope apparatus according to claim 1 wherein said illuminating means comprises a light source lamp for generating an illuminating light, a color separating filter for sequentially separating in time series this illuminating light into a plurality of color lights and a moving means for moving said color separating filter out of or into the light path of the illuminating light when said confirming signal is input.

8. An electronic endoscope apparatus according to claim 1 wherein said illuminating means comprises a light source lamp for generating an illuminating light and a adjusting means for adjusting the light amount of the illuminating light generated by said light source lamp when said confirming signal is input.

9. An electronic endoscope apparatus according to claim 7 wherein said signal processing means will output to said displaying means one color signal of a plurality of color signals produced from said electric signal when said color separating filter is moved out of the light path but will display a black and white moving picture in said displaying means by said one color signal while said color separating filter is moving and is out of the light path.

10. An electronic endoscope apparatus according to claim 8 wherein said signal processing means will output to said displaying means only a luminance signal produced from said electric signal when said light source lamp is adjusted in the light amount by said adjusting means and will display a black and white moving picture while the is being adjusted.

11. An electronic endoscope apparatus according to claim 1 wherein said signal processing means will output to said displaying means one color signal of a plurality of color signals produced from said electric signals and will display a black and white moving picture when said confirming signal is input.

12. An electronic endoscope apparatus according to claim 7 wherein said signal processing means has a still picture memory and a moving picture memory, will sequentially output the respective memories when said color separating filter is moved out of the light path and will simultaneously display on picture surface of said displaying means a color still picture image output from the still picture memory and a back and white moving picture image output from the moving picture memory while said color separating filter is moving and is out of the light path.

13. An electronic endoscope apparatus according to claim 7 wherein, with the movement of said color separating filter out of the light path, said signal processing means will repeatedly output to said displaying means the color signal produced from said electric signal before said color separating filter moves out of the light path and will display a color still picture image while said color separating filter is moving and is out of the light path.

14. An electronic endoscope apparatus according to claim 7 wherein said signal processing means will repeatedly output to said displaying means the color signal produced from said electric signal before said color separating filter moves while said color separating filter is moving out of or into the light path and will display in said displaying means a color still picture image while moving out of the light path, a black and white still picture image while moving into the light path and one color signal of a plurality of color signals produced from said electric signal while said color separating filter is out of the light path.

15. An electronic endoscope apparatus according to claim 8 wherein said brightness adjusting means is a flashing means repeatedly flashing said light source lamp.

16. An electronic endoscope apparatus according to claim 15 wherein, while said light source lamp flashes, said signal processing means will output to said displaying means only the luminance signal produced from said electric signal and will display a black and white moving picture.

17. An electronic endoscope apparatus according to claim 7 wherein said illuminating means further has a flashing means repeatedly flashing said light source lamp when said confirming signal is input.

18. An electronic endoscope apparatus according to claim 17 wherein said signal processing means will be synchronized with pulses generated by said flashing means to make the displayed picture image of said displaying means a still picture image while said color separating filter is moving out of the light path and is out of the light path and will make it a moving picture between said pulses.

19. An electronic endoscope apparatus according to claim 8 wherein said signal processing means has a memory part for memorizing the video signal produced from said electric signal and, when said light source lamp is adjusted in brightness by said light amount adjusting means, it will be inhibited to write a new video signal into said memory part, the already written-in video signal will be repeatedly output and a color still picture image will be displayed in said displaying means.

20. An electronic endoscope apparatus according to claim 7 wherein said signal processing means has a frame sequential type signal processing circuit and a simultaneous type signal processing circuit and, in case said confirming signal is not input, a video signal will be produced and output from said electric signal in said frame sequential type signal processing circuit and, in case said confirming signal is input, a video signal will be produced and output from said electric signal in said simultaneous type signal processing circuit.

21. An electronic endoscope apparatus according to claim 9 wherein said signal processing means has two groups of memory parts formed respectively of three frame memories alternately writing in and reading out.

22. An electronic endoscope apparatus according to claim 9 wherein said signal processing means has a memory part formed of a plurality of frame memories and this memory part writes into any one frame memory of the plurality of frame memories and at the same time reads out of another frame memory.

23. An electronic endoscope apparatus whereby, when a light emitted from an illuminating window provided in a tip part of an insertable part inserted into a body cavity is transmitted out of the body from within the body cavity, the position of said tip part will be confirmed from outside the body, comprising:
  an imaging means for providing an image of an inspected part obtained from an observing window provided in the tip part of said insertable part, and for converting this image to an electric signal and outputting it;
  an illuminating means for feeding an illuminating light to said imaging means and for adjusting the brightness of the illuminating light when a confirming signal directing the confirmation of the position of the tip part of said insertable part is input from outside the body;
  a signal processing means having a signal processing circuit for processing the electric signal obtained from said imaging means for producing a video signal and a memory part which can memorize said video signal, and for outputting a video signal as a moving picture signal in case said confirming signal is not input and memorizing said video signal in said memory part and repeatedly outputting the video signal as a still picture signal when said confirming signal is input; and
  a displaying means for receiving said video signal output by said signal processing means for displaying one of a moving picture and still picture image of the inspected part.

24. An electronic endoscope apparatus according to claim 1 wherein the confirming signal directing the confirmation of the position of the tip part of the insertable part is input by a switch.

25. An electronic endoscope apparatus according to claim 24 wherein said switch is provided in said imaging means.

26. An electronic endoscope apparatus whereby, when a light emitted from an illuminating window provided in a tip part of an insertable part inserted into a body cavity is transmitted out of the body from within the body cavity, the position of said tip part will be confirmed from outside the body, comprising:

an imaging means for producing an image of an inspected part obtained from an observing widow provided in the top part of said insertable part, and for converting this image to an electric signal and outputting it;

an illuminating means having a color separating filter for sequentially separating in time series an illuminating light into a plurality of color lights and capable of selectively feeding to said imaging means an illuminating light separated by said color separating filter or an illuminating light not separated by said color separating filter;

a signal processing means whereby said electric signal is process and, in case the illuminating light not separated by said color separating filter is fed to said imaging means, a video signal which is a black and white picture image signal and a video signal which is a color picture image signal will be output; and a displaying means for receiving a video signal which is a black and white picture image signal and a video signal which is a color picture image signal output by said signal processing means and simultaneously displaying the black and white picture image and color picture image.

27. An electronic endoscope apparatus according to claim 23, wherein the confirming signal directing the confirmation of the position of the tip part of the insertable part is input by a switch.

* * * * *